(12) United States Patent
Mounir et al.

(10) Patent No.: US 11,337,777 B2
(45) Date of Patent: May 24, 2022

(54) TOOTH CAPPING METHOD WITH AMELOGENIN

(71) Applicant: King Abdulaziz University, Jeddah (SA)

(72) Inventors: Maha M. F. Mounir, Jeddah (SA); Laila Ahmed Salim Bahammam, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/458,955

(22) Filed: Aug. 27, 2021

(65) Prior Publication Data
US 2021/0386518 A1 Dec. 16, 2021

Related U.S. Application Data

(63) Continuation of application No. 16/568,909, filed on Sep. 12, 2019.

(51) Int. Cl.
| | | |
|---|---|---|
| *A61C 5/30* | (2017.01) | |
| *A61C 5/77* | (2017.01) | |
| *A61K 6/69* | (2020.01) | |
| *A61K 6/898* | (2020.01) | |

(52) U.S. Cl.
CPC .......... *A61C 5/30* (2017.02); *A61C 5/77* (2017.02); *A61K 6/69* (2020.01); *A61K 6/898* (2020.01)

(58) Field of Classification Search
CPC ..................................................... A61C 5/30
See application file for complete search history.

(56) References Cited

U.S. PATENT DOCUMENTS

| | | | |
|---|---|---|---|
| 4,672,032 A | 6/1987 | Slavkin et al. | |
| 6,503,539 B2 * | 1/2003 | Gestrelius | A61L 24/108 424/549 |
| 7,304,030 B2 | 12/2007 | Lyngstadaas et al. | |
| 8,029,769 B2 * | 10/2011 | Lyngstadaas | A61K 8/64 424/49 |
| 2011/0256495 A1 | 10/2011 | Mounir et al. | |
| 2014/0023979 A1 | 1/2014 | Mounir | |
| 2016/0324728 A1 * | 11/2016 | Apicella | A61K 8/36 |
| 2018/0161394 A1 | 6/2018 | Mounir et al. | |

FOREIGN PATENT DOCUMENTS

| | | |
|---|---|---|
| CA | 2 413 253 A1 | 12/2001 |
| EP | 0 263 086 B1 | 12/1991 |
| EP | 0 337 967 B1 | 5/1993 |

OTHER PUBLICATIONS

Vandana J Rathva, "Enamel matrix protein derivatives: role in periodontal regeneration", Clinical, Cosmetic and Investigational Dentistry, vol. 3, 2011, pp. 79-92.

Maha M.F. Mounir, et al., "Recombinant Amelogenin Protein Induces Apical Closure and Pulp Regeneration in Open-apex, Non-vital Permanent Canine Teeth", J Endad. vol. 42, No. 3, Mar. 2016, pp. 402-412.

Maha M.F. Mounir, et al., "Characterization of the apical bridge barrier formed following amelogenin apexification", BMC Oral Health, vol. 18, No. 201, 2018, pp. 1-8.

* cited by examiner

*Primary Examiner* — Michael F Pepitone
(74) *Attorney, Agent, or Firm* — Oblon, McClelland, Maier & Neustadt, L.L.P.

(57) ABSTRACT

The invention relates to the application of a composition containing recombinant amelogenin and propylene glycol alginate ("PGA") on to cut dentin tubules followed by installation of a definitive restorative in a single visit.

8 Claims, 11 Drawing Sheets

Specification includes a Sequence Listing.

SEQUENCE LISTING

```
<160> NUMBER OF SEQ ID NOS: 7

<210> SEQ ID NO 1
<211> LENGTH: 793
<212> TYPE: DNA
<213> ORGANISM: Homo sapiens
<220> FEATURE:
<221> NAME/KEY: CDS
<222> LOCATION: (69)..(644)
<223> OTHER INFORMATION: Homo sapiens amelogenin X-linked (AMELX),
      transcript variant 1, mRNA

<400> SEQUENCE: 1
aaaggatcaa gcatccctga gtttcaaaca gaaacttgca ctgaatacat tcaaagaacc      60 atcaagaa atg ggg acc tgg att tta ttt gcc tgc ctc ctg gga gca gct     110
         Met Gly Thr Trp Ile Leu Phe Ala Cys Leu Leu Gly Ala Ala
         1               5                   10 ttt gcc atg cct cta cca cct cat cct ggg cac cct ggt tat atc aac     158
Phe Ala Met Pro Leu Pro Pro His Pro Gly His Pro Gly Tyr Ile Asn
15                  20                  25                  30 ttc agc tat gag gtg ctt acc cct ttg aag tgg tac cag agc ata agg     206
Phe Ser Tyr Glu Val Leu Thr Pro Leu Lys Trp Tyr Gln Ser Ile Arg
                35                  40                  45 cca ccg tac cct tcc tat ggt tac gag ccc atg ggt gga tgg ctg cac     254
Pro Pro Tyr Pro Ser Tyr Gly Tyr Glu Pro Met Gly Gly Trp Leu His
            50                  55                  60 cac caa atc atc ccc gtg ctg tcc caa cag cac ccc ccg act cac acc     302
His Gln Ile Ile Pro Val Leu Ser Gln Gln His Pro Pro Thr His Thr
        65                  70                  75 ctg cag cct cat cac cac atc cca gtg gtg cca gct cag cag ccc gtg     350
Leu Gln Pro His His His Ile Pro Val Val Pro Ala Gln Gln Pro Val
    80                  85                  90 atc ccc cag caa cca atg atg ccc gtt cct ggc caa cac tcc atg act     398
Ile Pro Gln Gln Pro Met Met Pro Val Pro Gly Gln His Ser Met Thr
95                  100                 105                 110 cca atc caa cac cac cag cca aac ctc cct ccg ccc gcc cag cag ccc     446
Pro Ile Gln His His Gln Pro Asn Leu Pro Pro Pro Ala Gln Gln Pro
                115                 120                 125 tac cag ccc cag cct gtt cag cca cag cct cac cag ccc atg cag ccc     494
Tyr Gln Pro Gln Pro Val Gln Pro Gln Pro His Gln Pro Met Gln Pro
            130                 135                 140 cag cca cct gtg cac ccc atg cag ccc ctg ccg cca cag cca cct ctg     542
Gln Pro Pro Val His Pro Met Gln Pro Leu Pro Pro Gln Pro Pro Leu
        145                 150                 155 cct ccg atg ttc ccc atg cag ccc ctg cct ccc atg ctt cct gat ctg     590
Pro Pro Met Phe Pro Met Gln Pro Leu Pro Pro Met Leu Pro Asp Leu
    160                 165                 170 act ctg gaa gct tgg cca tca aca gac aag acc aag cgg gag gaa gtg     638
Thr Leu Glu Ala Trp Pro Ser Thr Asp Lys Thr Lys Arg Glu Glu Val
175                 180                 185                 190 gat taa aagatcagaa gatgagaggg gaatgaatac ttcagatgct ttcaggagtg      694
Asp
```

```
acacaagaac acaatgattt ttgcttataa tcactttact tagcaaattc tgtaactaaa      754
aaagtaccat tagcagacaa taaaatgcat taaaaatca                             793
```

<210> SEQ ID NO 2
<211> LENGTH: 191
<212> TYPE: PRT
<213> ORGANISM: Homo sapiens

<400> SEQUENCE: 2

```
Met Gly Thr Trp Ile Leu Phe Ala Cys Leu Leu Gly Ala Ala Phe Ala
1               5                   10                  15

Met Pro Leu Pro Pro His Pro Gly His Pro Gly Tyr Ile Asn Phe Ser
            20                  25                  30

Tyr Glu Val Leu Thr Pro Leu Lys Trp Tyr Gln Ser Ile Arg Pro Pro
        35                  40                  45

Tyr Pro Ser Tyr Gly Tyr Glu Pro Met Gly Gly Trp Leu His His Gln
    50                  55                  60

Ile Ile Pro Val Leu Ser Gln Gln His Pro Thr His Thr Leu Gln
65                  70                  75                  80

Pro His His His Ile Pro Val Val Pro Ala Gln Gln Pro Val Ile Pro
                85                  90                  95

Gln Gln Pro Met Met Pro Val Pro Gly Gln His Ser Met Thr Pro Ile
            100                 105                 110

Gln His His Gln Pro Asn Leu Pro Pro Ala Gln Gln Pro Tyr Gln
        115                 120                 125

Pro Gln Pro Val Gln Pro Gln Pro His Gln Pro Met Gln Pro Gln Pro
    130                 135                 140

Pro Val His Pro Met Gln Pro Leu Pro Pro Gln Pro Pro Leu Pro Pro
145                 150                 155                 160

Met Phe Pro Met Gln Pro Leu Pro Pro Met Leu Pro Asp Leu Thr Leu
                165                 170                 175

Glu Ala Trp Pro Ser Thr Asp Lys Thr Lys Arg Glu Glu Val Asp
            180                 185                 190
```

<210> SEQ ID NO 3
<211> LENGTH: 802
<212> TYPE: DNA
<213> ORGANISM: Homo sapiens
<220> FEATURE:
<221> NAME/KEY: CDS
<222> LOCATION: (69)..(647)
<223> OTHER INFORMATION: Homo sapiens amelogenin Y-linked (AMELY),
      transcript variant 1, mRNA

<400> SEQUENCE: 3

```
agaggaccaa gcctccctgt gtagcacaaa gaaagtttct ctgaatatat ttaaagaacc       60 atcaagaa atg ggg acc tgg att ttg ttt gcc tgc ctt gtg gga gca gct      110
         Met Gly Thr Trp Ile Leu Phe Ala Cys Leu Val Gly Ala Ala
         1               5                   10 ttt gcc atg cct cta cca cct cat cct ggg cac cct ggt tat atc aac      158
Phe Ala Met Pro Leu Pro Pro His Pro Gly His Pro Gly Tyr Ile Asn
15                  20                  25                  30 ttc agc tat gag gtg ctc acc cct ttg aag tgg tac cag agc atg ata      206
Phe Ser Tyr Glu Val Leu Thr Pro Leu Lys Trp Tyr Gln Ser Met Ile
                35                  40                  45 aga cca cca tac tct tcc tat ggt tac gag ccc atg ggt gga tgg ctg      254
Arg Pro Pro Tyr Ser Ser Tyr Gly Tyr Glu Pro Met Gly Gly Trp Leu
            50                  55                  60
```

-continued

| | | |
|---|---|---|
| cac cac caa atc atc ccc gtg gtg tcc caa cag cac ccc ctg act cac<br>His His Gln Ile Ile Pro Val Val Ser Gln Gln His Pro Leu Thr His<br>               65                          70                     75 | 302 |
| acc ctg cag tct cat cac cac atc cca gtg gtg cca gct cag cag ccc<br>Thr Leu Gln Ser His His His Ile Pro Val Val Pro Ala Gln Gln Pro<br> 80                          85                                 90 | 350 |
| agg gtc cgc cag caa gca ctg atg cct gtt cct ggc cag caa tcc atg<br>Arg Val Arg Gln Gln Ala Leu Met Pro Val Pro Gly Gln Gln Ser Met<br>95                           100                       105                   110 | 398 |
| act cca acc caa cac cat cag cca aac ctc cct ctg cct gcc cag cag<br>Thr Pro Thr Gln His His Gln Pro Asn Leu Pro Leu Pro Ala Gln Gln<br>                     115                            120                        125 | 446 |
| ccc ttc cag ccc cag cct gtt cag cca cag cct cac cag ccc atg cag<br>Pro Phe Gln Pro Gln Pro Val Gln Pro Gln Pro His Gln Pro Met Gln<br>             130                          135                       140 | 494 |
| ccc cag cca cct gtg caa ccc atg cag ccc ctg ctg cca cag cca cct<br>Pro Gln Pro Pro Val Gln Pro Met Gln Pro Leu Leu Pro Gln Pro Pro<br>          145                        150                       155 | 542 |
| ctg cct cca atg ttc ccc ctg cgg ccc ctg ccc ccc ata ctt cct gat<br>Leu Pro Pro Met Phe Pro Leu Arg Pro Leu Pro Pro Ile Leu Pro Asp<br>     160                         165                       170 | 590 |
| ctg cat ctg gaa gct tgg cca gca aca gac aag acc aag cag gag gaa<br>Leu His Leu Glu Ala Trp Pro Ala Thr Asp Lys Thr Lys Gln Glu Glu<br>175                         180                       185                   190 | 638 |
| gtg gat taa aagaccagaa tatgagacag gaactgaagt aaacacttta<br>Val Asp | 687 |
| gttgctttca gggatgacac aagcacacaa tgattttgc ttacaatcac ttaacttagc | 747 |
| aaattctgta actaaaaatg taccaatagt agacaataaa atgttttaaa aatca | 802 |

<210> SEQ ID NO 4
<211> LENGTH: 192
<212> TYPE: PRT
<213> ORGANISM: Homo sapiens

<400> SEQUENCE: 4

Met Gly Thr Trp Ile Leu Phe Ala Cys Leu Val Gly Ala Ala Phe Ala
1               5                   10                  15

Met Pro Leu Pro Pro His Pro Gly His Pro Gly Tyr Ile Asn Phe Ser
            20                  25                  30

Tyr Glu Val Leu Thr Pro Leu Lys Trp Tyr Gln Ser Met Ile Arg Pro
        35                  40                  45

Pro Tyr Ser Ser Tyr Gly Tyr Glu Pro Met Gly Gly Trp Leu His His
    50                  55                  60

Gln Ile Ile Pro Val Val Ser Gln Gln His Pro Leu Thr His Thr Leu
65                  70                  75                  80

Gln Ser His His His Ile Pro Val Val Pro Ala Gln Gln Pro Arg Val
                85                  90                  95

Arg Gln Gln Ala Leu Met Pro Val Pro Gly Gln Gln Ser Met Thr Pro
            100                 105                 110

Thr Gln His His Gln Pro Asn Leu Pro Leu Pro Ala Gln Gln Pro Phe
        115                 120                 125

Gln Pro Gln Pro Val Gln Pro Gln Pro His Gln Pro Met Gln Pro Gln
    130                 135                 140

Pro Pro Val Gln Pro Met Gln Pro Leu Leu Pro Gln Pro Pro Leu Pro
145                 150                 155                 160

Pro Met Phe Pro Leu Arg Pro Leu Pro Pro Ile Leu Pro Asp Leu His
                165                 170                 175

```
Leu Glu Ala Trp Pro Ala Thr Asp Lys Thr Lys Gln Glu Glu Val Asp
            180                 185                 190

<210> SEQ ID NO 5
<211> LENGTH: 799
<212> TYPE: DNA
<213> ORGANISM: Mus musculus
<220> FEATURE:
<221> NAME/KEY: CDS
<222> LOCATION: (60)..(650)
<223> OTHER INFORMATION: Mus musculus MAME mRNA for amelogenin, complete
      cds

<400> SEQUENCE: 5
agcatccctg agcttcagac agaaactcac tgagcataca ctcaaagaac catcaagaa      59 atg ggg acc tgg att ttg ttt gcc tgc ctc ctg gga gca gct ttt gct     107
Met Gly Thr Trp Ile Leu Phe Ala Cys Leu Leu Gly Ala Ala Phe Ala
 1               5                  10                  15 atg ccc cta cca cct cat cct gga agc cct ggt tat atc aac tta agc     155
Met Pro Leu Pro Pro His Pro Gly Ser Pro Gly Tyr Ile Asn Leu Ser
             20                  25                  30 tat gag gtg ctt acc cct ttg aag tgg tac cag agc atg ata agg cag     203
Tyr Glu Val Leu Thr Pro Leu Lys Trp Tyr Gln Ser Met Ile Arg Gln
         35                  40                  45 ccg tat cct tcc tat ggt tac gaa ccc atg ggt gga tgg ctg cac cac     251
Pro Tyr Pro Ser Tyr Gly Tyr Glu Pro Met Gly Gly Trp Leu His His
     50                  55                  60 caa atc atc cct gtg ctg tct caa cag cat ccc ccg agt cac acc ctt     299
Gln Ile Ile Pro Val Leu Ser Gln Gln His Pro Pro Ser His Thr Leu
 65                  70                  75                  80 cag cct cat cac cac ctt ccc gtg gtg cca gct caa cag ccc gtg gcc     347
Gln Pro His His His Leu Pro Val Val Pro Ala Gln Gln Pro Val Ala
                 85                  90                  95 ccc cag caa cca atg atg cca gtt cct ggc cac cac tcc atg act cca     395
Pro Gln Gln Pro Met Met Pro Val Pro Gly His His Ser Met Thr Pro
            100                 105                 110 acc caa cac cat cag cca aac atc cct cca tcc gcc cag cag ccc ttc     443
Thr Gln His His Gln Pro Asn Ile Pro Pro Ser Ala Gln Gln Pro Phe
        115                 120                 125 cag cag ccc ttc cag ccc cag gcc att cca ccc cag tct cat cag ccc     491
Gln Gln Pro Phe Gln Pro Gln Ala Ile Pro Pro Gln Ser His Gln Pro
    130                 135                 140 atg cag ccc cag tca cct ctg cat ccc atg cag ccc ctg gca cca cag     539
Met Gln Pro Gln Ser Pro Leu His Pro Met Gln Pro Leu Ala Pro Gln
145                 150                 155                 160 cca cct ctg cct cca ctg ttc tcc atg cag ccc ctg tcc ccc att ctt     587
Pro Pro Leu Pro Pro Leu Phe Ser Met Gln Pro Leu Ser Pro Ile Leu
                165                 170                 175 cct gag ctg cct ctg gaa gct tgg cca gcg aca gac aag acc aag cgg     635
Pro Glu Leu Pro Leu Glu Ala Trp Pro Ala Thr Asp Lys Thr Lys Arg
            180                 185                 190 gaa gaa gtg gat taa aaaattcaga aaatgagaga accgaagtgg atactttggt    690
Glu Glu Val Asp
        195 tgttttttagg aataactcaa gaacacaatg atttgtgcct acaatcactt agtaaattct    750
gtaactaaaa ataagtatca ttagcagata ataaaatgtt tgaaaaatc                799

<210> SEQ ID NO 6
<211> LENGTH: 196
<212> TYPE: PRT
```

```
<213> ORGANISM: Mus musculus

<400> SEQUENCE: 6

Met Gly Thr Trp Ile Leu Phe Ala Cys Leu Leu Gly Ala Ala Phe Ala
1               5                   10                  15

Met Pro Leu Pro Pro His Pro Gly Ser Pro Gly Tyr Ile Asn Leu Ser
            20                  25                  30

Tyr Glu Val Leu Thr Pro Leu Lys Trp Tyr Gln Ser Met Ile Arg Gln
        35                  40                  45

Pro Tyr Pro Ser Tyr Gly Tyr Glu Pro Met Gly Gly Trp Leu His His
    50                  55                  60

Gln Ile Ile Pro Val Leu Ser Gln Gln His Pro Pro Ser His Thr Leu
65                  70                  75                  80

Gln Pro His His His Leu Pro Val Val Pro Ala Gln Gln Pro Val Ala
                85                  90                  95

Pro Gln Gln Pro Met Met Pro Val Pro Gly His His Ser Met Thr Pro
            100                 105                 110

Thr Gln His His Gln Pro Asn Ile Pro Pro Ser Ala Gln Gln Pro Phe
        115                 120                 125

Gln Gln Pro Phe Gln Pro Gln Ala Ile Pro Pro Gln Ser His Gln Pro
    130                 135                 140

Met Gln Pro Gln Ser Pro Leu His Pro Met Gln Pro Leu Ala Pro Gln
145                 150                 155                 160

Pro Pro Leu Pro Pro Leu Phe Ser Met Gln Pro Leu Ser Pro Ile Leu
                165                 170                 175

Pro Glu Leu Pro Leu Glu Ala Trp Pro Ala Thr Asp Lys Thr Lys Arg
            180                 185                 190

Glu Glu Val Asp
        195

<210> SEQ ID NO 7
<211> LENGTH: 11
<212> TYPE: PRT
<213> ORGANISM: Artificial Sequence
<220> FEATURE:
<223> OTHER INFORMATION: His tag

<400> SEQUENCE: 7

Arg Gly Ser His His His His His His Gly Ser
1               5                   10
```

TOOTH CAPPING METHOD WITH AMELOGENIN

CROSS-REFERENCE TO RELATED APPLICATIONS

The present application is a Continuation of U.S. application Ser. No. 16/568,909, pending, having a filing date of Sep. 12, 2019.

BACKGROUND OF THE INVENTION

Field of the Invention

The invention pertains to the fields of dentistry and dental reconstruction. More specifically, to preserving the natural, living teeth of a subject and avoiding procedures producing dead teeth or the need for prosthetic implants.

Description of the Related Art

The exposure or near exposure of living or vital pulp inside of a tooth to caries and other forms of decay, from trauma, such as from a broken or cracked tooth, or to a dental procedure that erodes the enamel and dentin can cause severe pain and the risk of inflammation and infection which can destroy the living or vital pulp. Unlike mechanical damage to a tooth in which pre-existing inflammation is not present, penetration of the pulp by caries results in microbial invasion of the pulp, resulting in pulpal inflammation and leaving the pulp less able to respond to the insult and heal; Murray P E, Windsor L J, Smyth T W, Hafez A A, Cox C F. Analysis of pulpal reactions to restorative procedures, materials, pulp capping, and future therapies. Critical Reviews in Oral Biology & Medicine. 2002; 13(6):509-520; Northwest Precedent. A survey of practitioner preference in direct pulp capping materials, 2007.

The morbidity associated with treating pulp exposures is consequential and often requires expensive and painful procedures such as root canal or endodontic therapy, tooth extraction, or prosthetic replacement of a tooth. However, the loss of vital pulp in a tooth results in the loss of tooth sensation, in the inability of a tooth to repair itself, and in a decreased lifespan for the tooth.

As an alternative to endodontic therapy or extraction or replacement of a damaged tooth, the tooth may be capped. Pulp capping involves placing a medicament on top of the exposed pulp tissue in an attempt to promote pulp healing and dentin repair; see tooth anatomy in FIG. 11 (prior art). A number of materials have been suggested for use in direct pulp capping, however, no one material seems to enjoy a significant preference among practitioners; Paine M L, White S N, Luo W, Fong H, Sarikaya M and Snead M L. Regulated gene expression dictates enamel structure and tooth function. Matrix Biol 2001; 20:273; Zeichner-David M. Is there more to enamel matrix proteins than biomineralization? Matrix Biol. 2001; 20:307). An ideal capping procedure or capping material would not only form a dentin bridge over the breach caused by caries or injury, but preserve the vitality and integrity of the living pulp inside of the tooth. Ideally, a capping procedure would only require a single visit to a dentist to repair and cap the tooth.

There are two types of capping: indirect capping and direct capping. When caries are in close proximity to the pulp, an indirect pulp cap can be performed. In this procedure, much of the infected and affected dentin is removed without exposing the pulp in a vital, healthy tooth. This is followed by the placement of a medicament (such as calcium hydroxide or a bioactive material) in order to promote the formation of tertiary dentin. Stepwise indirect capping involves cavity preparation to remove all carious enamel, but leaves carious dentin in place adjacent to the pulp chamber. A medicament is placed over the remaining caries, a provisional restoration is placed and the patient is scheduled for a second appointment. At the second visit, the provisional restoration and remaining caries are removed, and a definitive restoration is placed. The goal of a stepwise approach is to both promote the formation of tertiary dentin and change the environment within the tooth to prevent further progression of the carious lesion.

With a single-visit indirect pulp cap, as much of the carious lesion as possible is removed without inducing a pulpal exposure. A medicament is placed in the deepest aspect of the preparation, and a definitive restoration is placed. Unlike the stepwise approach, a single-visit excavation does not require a second visit to restore the tooth, and there is no risk of an inadvertent pulpal exposure when re-entry of the tooth occurs.

As long as the pulp is vital and asymptomatic, conventional indirect capping procedures can leave some decay near the pulp but cover the area with a bio-compatible material, such as a dentin bonding agents, resin glass ionomers, or calcium hydroxide, can stimulate the repair of the dentin and inhibit further decay. This incomplete removal of decay is not considered detrimental as long as the filling material completely seals the dentin from the bacterial environment of the oral cavity. However, this residual material can negatively impact the ability of the tooth to heal itself or regenerate.

A direct pulp cap is done on permanent teeth when the removal of deep decay results in exposing the pulp. If the pulp appears infected or symptomatic, a dentist may decide that removal of the living pulp is the best treatment option, for example as part of a root canal procedure. In situations where the pulp is vital and healthy, capping exposed pulp tissue with a material, such as calcium hydroxide, and providing a good seal with the filling material may solve the problem and prevent the need for further endodontic treatment. However, placement of conventional materials such as calcium hydroxide or mineral trioxide aggregate ("MTA") in indirect or direct capping procedures can also negatively impact the ability of a tooth to heal or regenerate as shown herein by the inventors.

Materials used for direct and indirect capping procedures include calcium hydroxide and mineral trioxide aggregate ("MTA") which is primarily calcium oxide in the form of tricalcium silicate, dicalcium silicate and tricalcium aluminate. These materials serve as a reservoir for calcium hydroxide and can provide a type of seal at the site of pulp exposure. However, MTA is highly soluble and can darken a treated tooth due to presence of iron in a gray MTA formulation. Moreover, it requires a second dental appointment for placement of a definitive restoration; Camilleri J, Montesin F E, Di Silvio L, Pitt Ford T R. The chemical constitution and biocompatibility of accelerated Portland cement for endodontic use. International Endodontics Journal. 2005; 38:834-842; Aeinehchi M, Eslami B, Ghanbariha M, Saffar A. Mineral trioxide aggregate (MTA) and calcium hydroxide as pulp-capping agents in human teeth: A preliminary report. International Endodontics Journal. 2002; 36:225-231; Tomson P, Grover L, Lumley P, Sloan A, Smith A, Cooper P. Dissolution of bio-active dentine matrix components by mineral trioxide aggregate. Journal of Dentistry. 2007; 35:636-642; de Souza Costa C, Duarte P, de Souza P, Giro E, Hebling J. Cytotoxic effects and pulpal response caused by a mineral trioxide aggregate formulation and calcium hydroxide. American Journal of Dentistry. 2008; 21:255-261; TJ Hilton. Keys to Clinical Success with Pulp Capping: A Review of the Literature. Oper Dent. 2009 September-October; 34(5): 615-62.

Mineral trioxide aggregate (MTA) is made of hydrophilic fine particles that harden in the presence of moisture or blood. It requires a working time of about 5 min and a hardening time that varies from 2 it and 45 min to 4 h according to the density of the air trapped during mixing and the dampness of the receiving site. The long hardening time reduces internal tensions and the incidence of marginal infiltration, but it forces to definitively fill the tooth in a subsequent dental visit or sitting.

Many conventional dental materials including MTA have distinct irritability and it has been observed that they exert adverse effects on different body organs. MTA contains heavy metals and releases arsenic and it has been found that MTA contained levels of arsenic that exceeded the levels (2 mg kg_1 of cement) recommended by international Standardization Organization (2007). When arsenic came in contact with blood during surgery, it was absorbed and carried by red blood cells, later leaving the blood stream and deposited in the liver and kidney. If the liver is not able to metabolize the arsenic, it becomes toxic and causes damage even in sublethal concentrations.

In contrast, as shown by the inventors r-amelogenin protein is biocompatible, it is composed of the same protein secreted in the oral cavity and it does not release toxic materials. Even if some particles become trapped in the pulp tissue, it will not cause adverse reactions. The pulp tissue capped with amelogenin proteins always restored and preserved the authentic pulp architecture in addition to forming a dentin bridge. No other capping material showed similar results Amelogenins are a family of proteins rich in proline, histidine, glutamine and leucine. Amelogenins are involved in forming a scaffold for mineral deposition and for production of cementum, dentin, and enamel; participate in hydroxyapatite crystallite formation, and form a matrix that regulates the subsequent crystallite growth. Moradian-Oldak J. Assembly, processing and control of crystal morphology Matrix Biology 2001; 20: 293); Fincham A G, Moradian-Oldak J, Simmer J P, Sart P, Lau E C, Diekwisch T and Slavkin H C. Self assembly of a recombinant amelogenin protein generates supramolecular structures. J Struct Biol 1994; 112:103.

Prior attempts have been made to use enamel matrix proteins These include the use recombinant amelogenin protein to induce apical (at base of a root of a tooth) closure and pulp regeneration in non-vital immature teeth in canines (Mounir, et al., J. Endod. 2016, 42(3):402-412); for apexification and root canal treatment of the premolar teeth of young dogs with amelogenin and PGA (Mounir, et al., US20140023979A1), and for regeneration of dentin (Lyngstadaas, et al., U.S. Pat. No. 7,304,030). Prior methods, such as those described by Mounir only cut the enamel, for example, Mounir only cuts the enamel in cervical region 7 and does not touch or cut dentin. Such procedures do not make deep cuts in the dentin which expose the inside of the dentinal tubules to the matrix material which penetrate the cytoplasm of the tubule to reach the odontoblast layer and the pulp tissue.

However, mixtures of amelogenin and PGA have not been previously used for dental capping or evaluated against conventional materials such as MTA. Surprisingly, the inventors found that a mixture of amelogenin and PGA placed on open healthy dentinal tubules accelerated dentin bridge formation and replenishment of dental pulp compared to the conventional material MTA. This procedure can form a dentin bridge, preserve authentic pulp and induce regenerative of pulp tissue in previously empty canals. Moreover, the inventors have found that a mixture of amelogenin and PGA can be effectively used for capping procedures requiring only a single visit.

BRIEF SUMMARY OF THE INVENTION

The invention relates to applying a composition containing recombinant amelogenin and propylene which is preferably performed in a single visit. This simplified procedure regenerates dentin and forms a dentin bridge over a breached pulp chamber and overtime provides an increasingly solid dentin foundation for the restorative. This method regenerates dentin faster, and replenishes vital pulp without leaving empty spaces or voids in pulp tissue better, than conventional procedures using capping materials such as MTA. Nonlimiting embodiments of the invention include the following.

A method for indirect or direct capping of a tooth in a subject having a damaged tooth that comprises, consists essentially of, or consists of applying a composition comprising amelogenin and propylene glycol alginate ("PGA") to a surface of a pulp-containing tooth comprising open dentinal tubules or exposed pulp. In many embodiments of the invention, deep cuts are made to dentin which expose the inside of the dentinal tubules to the matrix material which penetrate the cytoplasm of the tubule to reach the odontoblast layer and the pulp tissue. In one embodiment this method indirectly caps a damaged tooth by applying the composition to open dentinal tubules. In another embodiment, this method directly caps a damaged tooth by applying the composition to open dentin tubules and/or to exposed pulp. In preferred embodiments a final restorative is applied over the surfaces of the teeth treated with the amelogenin and PGA and can be applied during a single visit or on the same day or within a span not exceeding 24 hours to the dentist. It is not necessary to perform a stepwise cap which requires a second dental visit. Moreover, unlike conventional direct capping procedures using calcium hydroxide or MTA, the method as disclosed herein using amelogenin and PGA provides for rapid formation of a dentin bridge over a breach or near breach of the pulp chamber of a tooth and provides superior regeneration of vital pulp tissue.

In some embodiments of this method a subject's tooth has been exposed to mechanical trauma not associated with a dental procedure; or has been exposed to mechanical trauma associated with a dental procedure. It may be used to treat or repair various forms of dental trauma including enamel infarction, enamel fracture, enamel-dentine fracture, enamel-dentine fracture involving pulp exposure, or injuries including root fracture.

The composition used in the method disclosed above can contain amelogenin which comprises an amino acid sequence that is at least 75, 80, 85, 90, 95, 96, 97, 98, 99 or 100% identical to the amino acid sequence of SEQ ID NO: 2, 4 or 6 or a sequence that has at least 75, 80, 85, 90, 95, 96, 97, 98, 99 or 100% sequence identity to SEQ ID NOS: 2, 4 or 6 or a fragment thereof having at least 10, 15, 20, 25, 30, 35, 40, 45, 50, 55, 60, 70, 80, 90, 100, 110, 120, 130, 140, 150, 160, 170, 180 or >180 contiguous amino acid residues of the sequence. Preferably, the subject is a human and can be treated with a composition containing human amelogenin or a fragment thereof having at least 30 contiguous amino acid residues of the human amelogenin. However, in view of the conservation of amelogenin sequences, treatment with murine or other types of amelogenins may also be performed.

The composition used in the methods disclosed herein may contain 10, 20, 30, 40, 50, 60, or >60 mg of amelogenin per 1 cc of propylene glycol alginate vehicle, preferably from about 40 mg per 1 cc of PGA vehicle, or more preferably about 30 mg of amelogenin per 1 cc of PGA vehicle. In some embodiments, the composition will comprise, consist essentially of, or consist of amelogenin and PGA. The use of recombinant amelogenin permits one to eliminate the presence of other biological components that co-purify when amelogenin is isolated from a natural source thus providing an easily standardizable composition for use in dental or medical procedures.

Amelogenin may be present in a composition of the invention at a concentration ranging from 0.01, 0.02, 0.05, 0.1, 0.2, 0.5, 1, 2, 5, 10, 20, 30, 40, 50, 60, 70, 80, 90 or 100 mg/cc in combination with a vehicle containing PGA. This range includes all intermediate values and subranges.

A PGA vehicle may contain a concentration of PGA ranging from about 0.01, 0.02, 0.05, 0.1, 0.2, 0.5, 1, 2, 3, 4, 5 or >5 wt % PGA in water or other aqueous solution, preferably from about 2 to about 3 wt % based on the total weight of an aqueous solution containing the PGA in order to provide sufficient viscosity and fluidity to be easily combined with amelogenin and applied to dental surfaces. This range includes all intermediate values and subranges. In one embodiment, the PGA vehicle contains 20-40 mg of PGA in 1 $cm^3$ saline, more preferably about 30 mg of PGA in 1 $cm^3$ saline.

In other embodiments, the composition used in the methods disclosed herein will further comprise a remineralization agent selected from the group consisting of a material providing calcium ions, a material providing phosphorous ions, or a material providing fluoride ions. These materials include, but are not limited to calcium phosphates such as hydroxyapatite, tricalcium phosphate, or calcium monohydrogen phosphate, calcium hydroxide, calcium carbonate, arginine phosphate, sodium monofluorophosphate, or other salts containing calcium, phosphorous or fluoride ions. It may also include at least one non-amelogenin enamel matrix protein which may be purified from a natural source, such as from porcine teeth or recombinantly expressed.

In other embodiments the composition further comprises at least one bacteriostatic or bactericidal agent such as amoxicillin, metronidazole, penicillin, clarithromycin, or clindamycin.

The methods disclosed herein are preferably used on subjects is in need of regeneration of a dentin bridge and/or in need of preservation or regeneration of vital pulp without voids within the pulpal chamber of the tooth, such as subjects wishing to retain their living teeth and who opt to not undergo destructive dental procedures such as root canal surgery which removes and destroys living pulp.

In one embodiment, the subject is suffering from a subject suffering from amelogenesis imperfecta and said composition comprises a wild-type amelogenin to compensate for problems caused by the expression or presence of a mutant form of amelogenin.

Another embodiment of the invention is directed to a composition comprising human amelogenin and polyglycol alginate in a ratio of about 10 to 60 mg, preferably from about 20 mg to 40 mg amelogenin per ml of polyglycol alginate vehicle, in combination with (i) MMP-9, MMP-20, kallikrein or at least one other protease that cleaves or digests amelogenin; and/or in combination with (ii) amelogenin that has been at least partially digested by MMP-9, MMP-20, kallikrein 4, or at least one other protease that cleaves or digests amelogenin. A protease may be at any concentration sufficient to cleave amelogenin or to gradually cleave an applied dose of amelogenin over a period of 1, 2, 3, 4, 5, 6, 7, 8, 9, 10 or more weeks. Representative concentrations include 0.001, 0.002, 0.005, 0.01, 0.02, 0.05, 0.1, 0.2, 0.5, 1 or 2 wt % based on the total weight of the amelogenin and PGA composition. In some embodiments, proteases may be incorporated into a timed-release or modified-release dosage form to release the protease over a period of time such as over 4, 5, 6, 7, 8, 9, or 10 weeks.

An amelogenin and PGA composition as disclosed herein may include least one non-amelogenin enamel matrix protein, or may include a remineralization agent selected from the group consisting of a material providing calcium ions, a material providing phosphorous ions, or a material providing fluoride ions.

Another embodiment of the invention is directed to a kit for applying a composition comprising amelogenin and PGA comprising amelogenin, PGA, a device for mixing and/or applying the composition to open dentin tubules or to a surface having exposed pulp, and directions for use.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Figure 1:
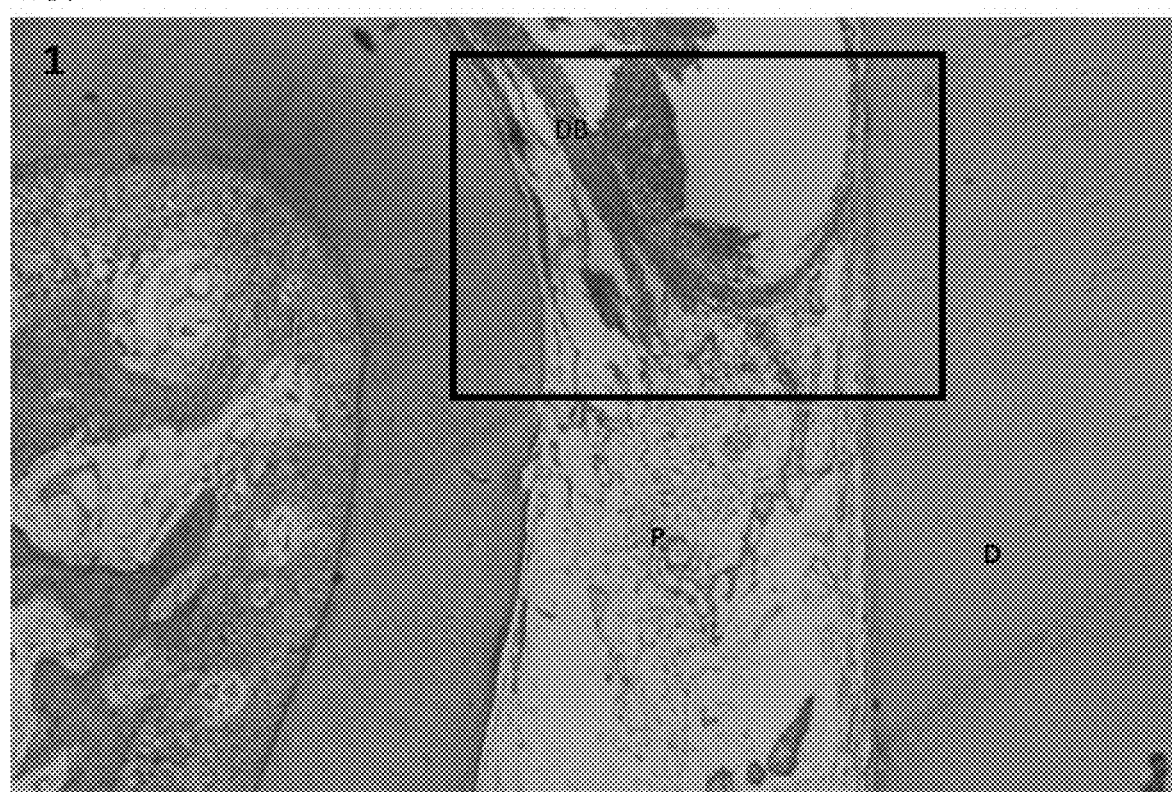
FIG. 1. Appearance of teeth treated with amelogenin-PGA after 10 days.

Abbreviations appearing in the figures: BD: dentin bridge; D: dentin; P: pulp, od: odontoblasts, V: voids; By: blood vessels; PD: predentin; PS: pulp space.

DETAILED DESCRIPTION OF THE INVENTION

A number of materials have been used in direct pulp capping procedures. However, conventional capping materials can negatively impact dentine regeneration and pulp tissue which are exposed during a capping procedure. Previously no one pulp material could induce the formation of dentin bridge and preserve vital pulp tissue exposed during a dental procedure.

The present invention provides an amelogenin composition that induces dentin bridge formation while simultaneously facilitating dentine regeneration and preserving pulp tissue thus avoiding the drawbacks associated with conventional capping materials such as calcium hydroxide and MTA. The invention also relates to a method for preparing the active enamel matrix material for the preparation of a pharmaceutical composition capable of regenerating dentin and preserving pulp vitality following dental procedures involving exposure of vital dental pulp tissue.

Advantageously, the amelogenin-PGA composition and its method of use for protecting and restoring viability to damaged teeth advantageously relate to the characteristic that amelogenin and PGA are easily mixed and applied. The invention provides a natural way to repair and restore viability in damaged teeth because amelogenin is a protein involved in the natural growth and enamelization of teeth and thus can interact with other natural components of teeth without the high risk of toxicity associated with some artificial materials. For example, the inventors have shown that amelogenin induces minimal inflammatory reactions when placed over exposed pulp tissue and preservation rather than damage to pulp tissue. The inventors further showed that amelogenin induces healing of the damaged tooth by inducing formation of tertiary dentine mineralized tissue barrier between the pulp chamber and overlying dental structures.

The invention preserves the underlying pulp tissue which becomes continuous with no internal voids and fills the complete pulp chamber and root canal space in contrast to similar treatments with MTA and the pulp regenerated after treatment with amelogenin-PGA composition appears to the same or similar to original pulp. The inventors demonstrate that a mixture of amelogenin and PGA can be effectively used as a dental pulp capping material which quickly regenerates a dentin bridge over a breach or near breach in the pulp chamber of a tooth. They also show that capping with a mixture of amelogenin and PGA provides a superior degree of protection to pulp tissue in a damaged and capped tooth and prevents the formation of voids seen in teeth capped with conventional agents like MTA. The method according to the invention preserves pulp tissue and a tooth's vitality as well as its ability to sense heat or cold and other sensations and respond to such stimuli. Preservation of the pulp tissue preserves the tooth's ability to repair itself, prevents the weakening of the tooth structure, such as weakening caused by root canal surgery, that increase the risk of fracture and loss of a repaired tooth. Moreover, the method as disclosed herein prevents pulp inflammation (pulpitis) and subsequent irreversible pulpitis and degeneration of the dental pulps that would otherwise require additional dental treatments such as pulpectomy, pulpotomy or root canal treatments ("RCT").

Subjects of treatment. A subject is typically a person with dental trauma, especially trauma which exposes vital pulp or dentine. Trauma may be to non-permanent or permanent teeth, such as one or more molars, canine teeth, or incisors. Preferably, treatment of the subject with amelogenin and PGA composition disclosed herein is performed on a tooth containing vital pulp or asymptomatic pulp where the tooth has not been subjected to a pulpectomy (complete removal of pulp) or pulpotomy (partial removal of pulp).

Teeth include any one of the 32 human teeth identified by the universal numbering system as well as human baby teeth. A baby tooth may be capped in order to provide time for a healthy, properly aligned permanent tooth to erupt. Human subjects include both males and females and children and adults, for example; children less than 1, 2, 3, 4, 5, 6, 7, 8, 9, 10, 11, 12, 13, 14, 15, 16, 17, or 18 years old and adults of at least 18, 19, 20, 21, 25, 30, 35, 40, 45, 50, 55, 60, 65, 70, 75, 80, 85, 90, 95, 100 or >100 years old.

Other subjects include non-human mammals or other animals having teeth, such as a dog, cat, horse, or other domesticated or wild animals, such as gorillas, orangutans, chimpanzees and other simians, lions, tigers, and cheetahs and other cats, bears, polar bears, pandas, elephants, zebras, giraffes, meerkats, goats, sheep, llamas, camels, etc. The term "tooth" as used herein also includes tusks, such as those of elephants, wild pigs and walruses. Preferably, the amelogenin used in the composition disclosed herein is a homologous amelogenin derived from the same species of animal as the subject being treated, though in some embodiments, a xenogenic amelogenin such as one having at least 90, 95 or 99% sequence identity to amelogenin of the subject being treated, may be used due to the highly conserved nature of amelogenins.

Disinfection/Cleaning. Exposed dental surfaces may be cleaned and/or disinfected, for example, by removal of decayed enamel or dentine, with a sterile or an antiseptic wash, sonic energy, UV or light exposure, or mechanically by complete or partial extraction prior to treatment with amelogenin and PGA. Damaged, unstable, or carried enamel or dentin can removed prior to application of the composition of the invention preferably without aggravating any breach in the pulp chamber.

Direct and indirect capping. The method as disclosed herein may be used for both direct and indirect pulp capping. Pulp capping is a dental procedure used to prevent the death of dental pulp after an exposure or near exposure, by placing a protective material or dressing over the pulp. This exposure may be due to a mechanical trauma after an accident or tooth fracture such as a fractured or broken tooth, infected tooth or deep cavity; or the pulp may be exposed during a cavity cutting procedure in the dental office or as a result of repeated dental procedures.

Indirect capping with a composition as disclosed herein is typically used for treating a tooth without any exposed pulp tissue, for example, when bacterial decay has reached near to the pulpal chamber, but not penetrated it, and causes inflammation or threatens the survival of the tooth. Direct capping procedure is employed where pulp has already been exposed or almost exposed and the composition as disclosed herein is applied over the exposed or nearly exposed pulp tissue such as on the crown of a tooth. A direct pulp cap is usually done on permanent teeth when the removal of deep decay results in exposing the pulp. In situations where the pulp is vital and healthy, capping exposed pulp tissue with an amelogenin and PGA composition as disclosed herein, and providing a good seal with the filling material may solve the problem and prevent the need for further endodontic treatment.

In some embodiments, the amelogenin and PGA composition of the invention may be loaded into separate syringes or other devices for administering dental compositions and a delivered in to a tooth through a single nozzle or needle that mixes them. In other embodiments, the amelogenin and vehicle are premixed and the administered as a mixed composition into or over a tooth. In some embodiments, the method of the invention does not involve dispensing the amelogenin composition to near cut cervical enamel, to the root apex, or to periapical tissues around the root apex.

In some embodiments, after capping a tooth with the composition as described herein, the material is permitted to set for a period of 5, 10, 15, 30, 45, 60, 90, 120 or 180 minutes prior to completion of the dental procedure, for example, by placement of a permanent restorative, and dismissal of the patient.

Amelogenin. As used herein, this term unless otherwise specified includes human and non-human unprocessed, processed full-length amelogenin without its signal peptide, as well as amelogenin fragments such as those resulting from the action of enzymes or proteases. Amelogenin M180 is a form of murine amelogenin. Representative amelogenin nucleic acid/amino acid sequences include those of human AMELX (SEQ ID NOS: 1 and 2), human AMELY (SEQ ID NOS: 3 and 4) and murine amelogenin (SEQ ID NOS: 5 and 6).

Natural amelogenins are synthesized from alternatively spliced mRNAs, ranging in size from 5 to 28 kDa. These proteins are further processed at both their C- and N-termini by matrix metalloproteinase 20 (MMP20), to form many smaller peptide fragments, including a 23-kDa amelogenin (Amg23), a 5-kDa tyrosine-rich amelogenin peptide (TRAP), and a 5.4-kDa leucine-rich amelogenin peptide (LRAP). The Amg23 and TRAP are formed from a full-length amelogenin (Amg25), while the LRAP is generated from an alternatively spliced LRAP precursor, description of amelogenin fragments and proteases acting on amelogenin are incorporated by reference to Fincham et al., Biosci Rep. 1981 October; 1(10):771-8; Gibson, et al., Biochem Biophys Res Commun. 1991 Feb. 14; 174(3):1306-12; Fincham and Moradian-Oldak, Biochem Biophys Res Commun. 1993 Nov. 30; 197(1):248-55; and Connect Tissue Res. 1995; 32(1-4):119-24; or Moradian-Oldak et al., Arch Oral Biol. 1994 August; 39(8):647-56.

The sequence of naturally produced amelogenin is typically divided into three prominent amino acid domains: a hydrophobic tyrosine-rich N-terminal domain, called the tyrosine-rich amelogenin peptide (TRAP); the central proline-rich region, which is hydrophobic and primarily composed of X-Y-proline (where X and Y are often glutamine) repeat motifs; and the hydrophilic C-terminal domain. The N- and C-terminal region amino acid sequences are highly conserved among mammalian species, suggesting that these segments play important roles in enamel development and mineralization. The native amelogenin contains a single phosphate group on serine-16 that is presumed to be involved in amelogenin-calcium phosphate interactions and contribute to the ability of amelogenin to stabilize the precursor amorphous calcium phosphate. The primary sequence is enriched with disorder-promoting residues, such as Pro (P), Gln (Q), Glu (E), Arg (R), and Lys (K), leading to the intrinsically labile nature of the protein.[4,5] Amelogenin belongs to the class of intrinsically disordered or unstructured proteins (IDPs). Unlike folded proteins, IDPs lack regular secondary or tertiary structure but are capable of transforming into a folded state following interactions with their targets and as part of their overall function. Full-length recombinant amelogenin molecules can spontaneously self-assemble into nanospheres under pH=8 conditions in the absence of calcium-phosphate. The inventors believe that the nanospheres were formed through intermolecular hydrophobic interactions when the hydrophilic segment of each molecule was exposed on the surface of the nanospheres. The nanospheres were then proposed to be the basic structural entities of the developing enamel extracellular matrix and to play a crucial function in enamel biomineralization.

Recombinant amelogenins for incorporation into an amelogenin and PGA composition can be synthesized from cDNA corresponding to the RNAs encoding amelogenin and its fragments by methods well known in the art, such as the cDNA cloning procedures described by Green, et al., *Molecular Cloning: A Laboratory Manual* (Fourth Edition, Cold Spring Harbor Press. 2014 (incorporated by reference) or using commercially available cloning kits, such as PCR cloning kits and reagents and other molecular biological materials, available from ThermoFisher Scientific (https://_www.thermofisher.com/us/en/home/brands/thermo-scientific/molecular-biology/thermo-scientific-molecular-cloning.html?s_kwcid=AL!3652!10!767597155543321767 59737462825&ef_id=XEeKuQAAEq iq9BGW: 20190503151725:s, last accessed May 3, 2019, incorporated by reference). In one embodiment recombinant poly-(histidine)-tagged proteins were expressed and recovered. These, recombinant amelogenin proteins were prepared with the expression vector pQE30 (QIAGEN Inc., Valencia, Calif.) and purified with a poly-(histidine) amino terminus, as previously described by Moradian-Oldakm et al., J., Struct. Biol. 131(1):2737 (2000) and Viswanathan, et al., J. Periodontaol 74(10):1423-31 (2003) both incorporated by reference. Recombinant poly-histidine-tagged murine 180 amino acid long amelogenin (rp(H) M180) is identical to the authentic mouse full-length amelogenin except for the inclusion of an amino-terminal peptide sequence (RGSHHHHHHGS)(SEQ ID NO: 7) used for affinity purification of the bacterially produced protein. The entire DNA fragment within the pQE30 vector was subjected to nucleotide sequence determination to ensure that no errors were generated during the DNA amplification procedures and that the construct was correctly engineered. Recombinant proteins were prepared and purified using nickel-nitrilotriacetic acid (Ni-NTA) metal-affinity chromatography matrices (Qiagen, Valencia, Calif.).

The major fraction of the enamel matrix proteins is composed of amelogenins, a family of hydrophobic proteins that account for more than 90% of the organic constituents of the enamel matrix. Unless otherwise specified the term amelogenin includes full-length amelogenin as well as processed forms of amelogenin such as amelogenin fragments as well as longer proteins such as an amelogenin comprising a signal peptide, a FLAG or HIS or other tag, or another exogenous amino acid sequence. It also includes variant amelogenin proteins such as those having at least 90, 95, 99 or <100% sequence identity to an amelogenin amino acid sequence disclosed herein as well as variants having 1, 2, 3, 4, 5, 6, 7, 8, 9, 10 or more deletions, additions or substitutions of amino acid residues to a known amelogenin sequence.

BLASTN may be used to identify a polynucleotide sequence having at least 70, 75, 80, 85, 90, 95, 96, 97, 98, 99, <100, or and 100% (or any intermediate %) sequence identity to a reference polynucleotide, such as a nucleic acid, such as cDNA or mRNA encoding an amelogenin as disclosed herein. A representative BLASTN setting optimized to find highly similar sequences uses an Expect Threshold of 10 and a Wordsize of 28, max matches in query range of 0, match/mismatch scores of 1/–2, and linear gap cost. Low complexity regions may be filtered/masked. Default settings are described by and incorporated by reference to http://_blast.ncbi.nlm.nih.gov/Blast.cgi?PROGRAM=blastn&BLAST_PROGRAMS=megaBlast&PAGE_TYPE=BlastSearch&SHOW_DEFAULTS=on&LINK_LOC=blasthome (last accessed May 3, 2019).

BLASTP can be used to identify an amino acid sequence having at least 70%, 75%, 80%, 85%, 87.5%, 90%, 92.5%, 95%, 96, 97.5%, 98%, 99%, <100% or 100% (or any intermediate %) sequence identity or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Default settings for BLASTP are described by and incorporated by reference to: http://_blast.ncbi.nlm.nih.gov/Blast.cgi?PROGRAM=blastp&PAGE_TYPE=BlastSearch&LINK_LOC=blasthome (last accessed May 3, 2019).

Amelogenin compositions. One or more of amelogenin or its protein fragments may be incorporated into an amelogenin and PGA composition according to the invention.

Typically, the composition of the invention will comprise full-length amelogenin, though in some embodiments it will comprise or consist essentially of an amelogenin fragment or a mixture of full-length and amelogenin fragments in the same weight proportion to PGA as described for full length amelogenin. Such a mixture may contain 0.1, 0.2, 0.5, 1, 2, 5, 10, 20, 30, 40, 50, 60, 70, 80, 90, 95, 98, 99, 99.9 to <100% of full-length amelogenin and 99.9, 90, 80, 70, 60, 50, 40, 30, 20, 10, 5, 2, 1, 0.5, 0.2, 0.1 to <0.1 wt % one or more amelogenin fragments. In other embodiments, the composition may comprise full-length recombinant amelogenin and MMP20 or another protease that processes full-length amelogenin into smaller fragments.

The amelogenins, which are the hydrophobic constituents of the enamel matrix proteins, aggregate and become almost insoluble at physiologic pH and temperature. They can be dissolved in an acidic or alkaline pH environment and at low temperature. A suitable formulation should thus have a non-neutral pH and allow for gradual reprecipitation of the matrix when physiologic conditions are re-established.

An amelogenin composition according to the invention may contain one or more pharmaceutically acceptable excipients and be in form of a solid, semi-solid or liquid composition including powders, granules, granulates, capsules, agarose or chitosan beads, tablets, pellets, microcapsules, microspheres, nanoparticles, or freeze-dried powders, granules, granulates or pellets, gels, hydrogels, pastes, solutions, dispersions, suspensions, emulsions, or mixtures.

The compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988. Apart from the amelogenin, a pharmaceutical composition for use according to the invention may comprise pharmaceutically acceptable excipients. A pharmaceutically acceptable excipient is a substance which is substantially harmless to the individual to which the composition is to be administered. Such an excipient normally fulfils the requirements given by the national health authorities. Official pharmacopoeias such as e.g. the British Pharmacopoeia, the United States of America Pharmacopoeia and The European Pharmacopoeia set standards for pharmaceutically acceptable excipients. The choice of a pharmaceutically acceptable excipient in a composition for use according to the invention and the optimum concentration thereof cannot generally be predicted and must be determined on the basis of an experimental evaluation of the final composition. However, a person skilled in the art of pharmaceutical formulation can find guidance in "Remington's Pharmaceutical Sciences", $21^{st}$ Edition, Mack Publishing Company, Easton, 2005. The pharmaceutically acceptable excipients may include solvents, buffering agents, preservatives, chelating agents, antioxidants, stabilizers, suspending agents and gel-forming agents. Examples of solvents are water, alcohols, or other hydrophilic or etheric solvents such as weak acids with a pH of about 5.5-6.0 facilitating the subsequent application of filling materials in the tooth. Examples of buffering agents are citric acid, acetic acid, tartaric acid, lactic acid, hydrogenphosphoric acid, and diethylamine. Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, benzalkonium chloride, and benzylalcohol, or mixtures of preservatives. Examples of antioxidants are butylated hydroxy anisole (BHA), ascorbic acid and derivatives thereof, tocopherol and derivatives thereof, cysteine, and mixtures thereof. Examples of suspending agents are celluloses and cellulose derivatives such as carboxymethyl cellulose, hydroxyethylcellulose, hydroxypropylcellulose, hydroxypropylmethylcellulose, microcrystalline cellulose (e.g. Avicel® RC 591), carrageenan, acacia gum, arabic gum, tragacanth, and mixtures thereof. Examples of gel bases or viscosity-increasing agents are liquid paraffin, polyethylene, fatty oils, colloidal silica or aluminum, zinc soaps, glycerol, propylene glycol, tragacanth, carboxyvinyl polymers, magnesium-aluminum silicates, Carbopol™, hydrophilic polymers such as starch or cellulose derivatives such as carboxymethylcellulose, hydroxyethylcellulose and other cellulose derivatives, water-swellable hydrocolloids, carragenans, hyaluronates, and alginates including propylene glycol alginate. Examples of powder components include alginate, collagen or lactose. Normally, powders intended for application on dental pulps must be sterile and the particles present must be micronized. Examples of other excipients are polymers such as carmelose, sodium carmelose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and chitosans. Suitable compositions for use according to the invention may also be presented in the form of suspensions, emulsions or dispersions. Such compositions can contain the active enamel substance in admixture with a dispersing or wetting agent, suspending agent, and/or one or more preservatives and other pharmaceutically acceptable excipients. Suitable dispersing or wetting agents are, for example, naturally occurring phosphatides, e.g., lecithin, or soybean lecithin; condensation products of ethylene oxide with a fatty acid, a long chain aliphatic alcohol, or a partial ester derived from fatty acids and a hexitol or a hexitol anhydride, for example polyoxyethylene stearate, polyoxyethylene sorbitol monooleate, or polyoxyethylene sorbitan monooleate.

Enamel matrix and other proteins. Other proteins which may be incorporated into an amelogenin and PGA composition as disclosed herein include enamelins, amelins, ameloblastin, sheathlin, tuftelins, tuft proteins, dentinsialoprotein, dentinsialophosphoprotein, serum proteins, and salivary proteins. The second largest component of the enamel matrix protein is the enamelins. Enamelins have been found to contain serum proteins, and the more general term "non-amelogenin" is now commonly used to describe this high molecular weight fraction, which includes proline-rich enamelin, tuftelin, and tuft proteins.

The composition of the invention may include, in addition to one or more amelogenins, any of the non-amelogenin enamel matrix proteins, for example, from 0.1, 0.2, 0.5, 1, 2, 5, 10 or >10 wt % based on the weight of the amelogenin composition.

Other ingredients. In some embodiments, the amelogenin and PGA composition of the invention will further include, or be further admixed with, at least 0.01, 0.02, 0.05, or 0.1 wt % based on a total weight of the composition, a protease, such as MMP20, that processes amelogenin, or with at least 0.01, 0.02, 0.05, 0.1, 0.2, 0.5, 1, 2, 5, 10 or 20 wt % agents such as one or more of tricalcium silicate, dicalcium silicate, tricalcium aluminate, tetracalcium aluminoferrite, calcium sulfate, and bismuth oxide, which are also ingredients in MTA. However, in many embodiments, the composition as disclosed herein consists of, or consists essentially of an amelogenin and PGA, without other capping agents.

Alginates and thickeners. In a preferred embodiment, the amelogenin composition described herein contains an alkylene glycol alginate, such as propylene glycol alginate ("PGA"). In some embodiments, the alkylene glycol alginate is formed from incomplete esterification of alginic acid, whereby some of the carboxyl groups of alginic acid or salts thereof are esterified with an alkylene oxide, while the remainder remain free or are neutralized with an appropriate alkali base. The alkylene glycol alginate may be a 'low esterification type', wherein less than 60%, preferably less than 50%, preferably less than 40% of the total number of carboxyl groups of alginic acid are esterified with an alkylene oxide(s) such as propylene glycol, the remaining groups being either free or neutralized with a base. In preferred embodiments, the alkylene glycol alginate is a 'high esterification type' where at least 60%, preferably at least 70%, preferably at least 75%, preferably at least 80%, and up to 90%, preferably up to 85% of a total number of carboxyl groups present in alginic acid or salts thereof are esterified with the alkylene oxide(s) to form the alkylene glycol alginate.

In some embodiments, the alkylene glycol alginate is formed using one or more alkylene oxides having 2 to 6 carbon atoms, preferably 3 to 4 carbon atoms, more preferably 3 carbon atoms. Suitable alkylene oxides specifically contemplated are ethylene oxide, propylene oxide, 1,3-epoxypropane, 1,2-epoxybutane, 2,3-epoxybutane, 1,2-epoxy-2-methylpropane, 1,2-epoxypentane, and 1,2-epoxyhexane, mixtures thereof, as well as any other alkylene oxide known by those of ordinary skill in the art as being appropriate for the preparation of alkylene glycol alginates. Among these alkylene oxides, propylene oxide and butylene oxide are preferred, more preferably propylene oxide.

Propylene glycol alginate is an emulsifier, stabilizer, and thickener used in food products. Chemically, propylene glycol alginate is an ester of alginic acid, which is derived from kelp. Some of the carboxyl groups are esterified with propylene glycol, some are neutralized with an appropriate alkali, and some remain free. However, in alternative embodiments, amelogenin may be combined at the same weight ratios as disclosed herein for PGA with one or more other thickeners.

In preferred embodiments, the alkylene glycol alginate employed herein is propylene glycol alginate (PGA). Propylene glycol alginate is a good thickener which exhibits slight pseudoplastic behavior. Propylene glycol alginates are broken down into grades based on viscosity and esterification levels (i.e., the percentage of esterified carboxyl groups described heretofore), and any grade of propylene glycol alginate may be utilized. Within the category of standard esterification types (e.g., less than 60% of carboxyl groups esterified), the propylene glycol alginate may have the following grades (based on viscosity ranges of a 1 wt. % solution at 20° C.): "LVC" (70 to 170 mPa·s); or "HVC" (200 to 600 mPa·s). Within the category of high esterification types (e.g., 60 to 90% of carboxyl groups esterified), the propylene glycol alginate may have the following grades (based on viscosity ranges of a 1 wt. % solution at 20° C.): "LLV" (15 to 35 mPa·s); "NLS-K" (30 to 60 mPa·s); "LV" (60 to 100 mPa·s); "MV" (100 to 150 mPa·s); and "HV" (150 to 250 mPa·s).

In preferred embodiments, the propylene glycol alginate utilized herein is an "HV" grade, i.e., is of a high esterification type having a viscosity of at least 150 mPa·s, preferably at least 175 mPa·s, preferably at least 200 mPa·s, and up to 250 mPa·s, preferably up to 225 mPa·s, preferably up to 215 mPa·s.

Propylene glycol alginates are available for example from Kimica Corp. under the tradename KIMILOID, for example, KIMILOID HV.

Most preferably, PGA is used in combination with amelogenin in a composition according to the invention. However, in some alternative embodiments, other thickeners may be used, especially thickeners which are biodegradable or metabolizable. Other thickeners include alginic acid, sodium alginate, potassium alginate, ammonium alginate, calcium alginate, polysaccharides derived from red or brown algae; PEG, agar, carrageenan, locust bean gum, xanthan, acacia, pectin, gelatin, and various cellulosics, sulfonates, and saccharides.

Amelogenesis imperfecta. A subject may express an isotype of a normal or wild-type amelogenin, which is associated with harder and/or not discolored teeth, or express a mutated form of amelogenin, such as one having T211 or P40T substitutions in the amelogenin sequence, which is associated with amelogenesis imperfecta causing the tooth to be hypomineralized and to have a brown discoloration. Such a subject may have a tooth partially restored, capped or otherwise treated using a composition containing a normal wild-type form of amelogenin, a mixture of wild-type and mutated amelogenin, or with a composition containing a mutated form of amelogenin. For a subject expressing a non-wild-type form of amelogenin, such as a mutant form that forms softer or discolored teeth or a form of amelogenin associated with amelogenesis imperfecta, direct or indirect capping may be performed using a composition comprising wild-type amelogenin in order to compensate for negative effects of the mutant form of amelogenin. For example, a subject suffering from amelogenesis imperfecta can have a soft or discolored tooth hardened and whitened by capping with a wild-type amelogenin. A mixture of wild-type and mutant amelogenin may contain a weight ratio of wild-type amelogenin to mutant amelogenin of 100:1, 50:1, 20:1, 10:1, 5:1, 2:1, 1:1, 1:2, 1:5, 1:10, 1:20, 1:50 or 1:100. In some embodiments, the amelogenin is full-length amelogenin. In other embodiments, at least one form of processed or truncated full-length amelogenin may be used.

Restoration materials. After application of the amelogenin-PGA composition of the invention on portions of teeth containing open dentin tubules or that expose pulp, a restorative is added to seal the tooth. It cures extremely hard and is very wear resistant. As a true glass ionomer, it chemically bonds to tooth structure, has a tooth-like coefficient of thermal expansion and releases significant levels of rechargeable fluoride. Other restorative materials include precious metal alloys such as gold, gold alloys, gold-platina alloy, silver-palladium alloy, cobalt-chrome alloy, nickel-chroma alloy; amalgam, such as silver amalgam or high copper dental amalgam; direct gold; composite resin, such as BISMA or UDMA or TEGMA; glass ionomer cement; porcelain, such as glass-bonded porcelain, lithium disilicate glass ceramic and phase stabilized zirconia. One example, of a restorative is GC Fuji IX GP which is a fluoride releasing alternative to expensive compomers and composites and in many cases, amalgam. In some embodiments, calcium hydroxide and bioceramic material are used.

EXAMPLES

Exposure of vital dental pulp, either accidentally or by design, is a complication commonly seen in dental practice. Preserving the dental pulp or part of it in a healthy state is important in treating teeth with exposed vital pulp. To test the effects of exposing vital dental pulp to the amelogenin and PGA composition of the invention, the following experiments were conducted.

Recombinant amelogenin was produced essentially as described by Moradian-Oldak J, Paine M L, Lei Y P, et al. Self-assembly properties of recombinant engineered amelogenin proteins analyzed by dynamic light scattering and atomic force microscopy. J Struct Biol 2000; 131:27-37; Viswanathan H L, Berry J E, Foster B L, et al. Amelogenin: a potential regulator of cementum-associated genes. J Periodontol 2003; 74:1423-31 (each incorporated by reference). Recombinant poly-histidine-tagged murine 180 amino acid long amelogenin (rp(H) M180) is identical to the authentic mouse full-length amelogenin except for the inclusion of an amino-terminal peptide sequence (RGSHHHHHHGS)(SEQ ID NO: 7) used for affinity purification of the bacterially produced protein. Briefly, recombinant amelogenin proteins comprising a polyhistidiine amino terminus were prepared with the expression vector pQE30 (QIAGEN Inc, Valencia, Calif.) and affinity purified using nickel nitrilotriacetic acid metal-affinity chromatography matrices (QIAGEN Inc).

Propylene glycol alginate vehicle as used in these experiments contained 30 mg of propylene glycol aliginate in 1 $cm^3$ of saline. Approximately 1 mL propylene glycol alginate vehicle was mixed with 30 mg recombinant amelogenin protein powder (rp[H] M180) 15 minutes before use. The mixture was placed on the exposed pulp to be compared with MTA capping material. PGA powder concentration was determined by the manufacturer of r-amelogenin.

Figure 2:
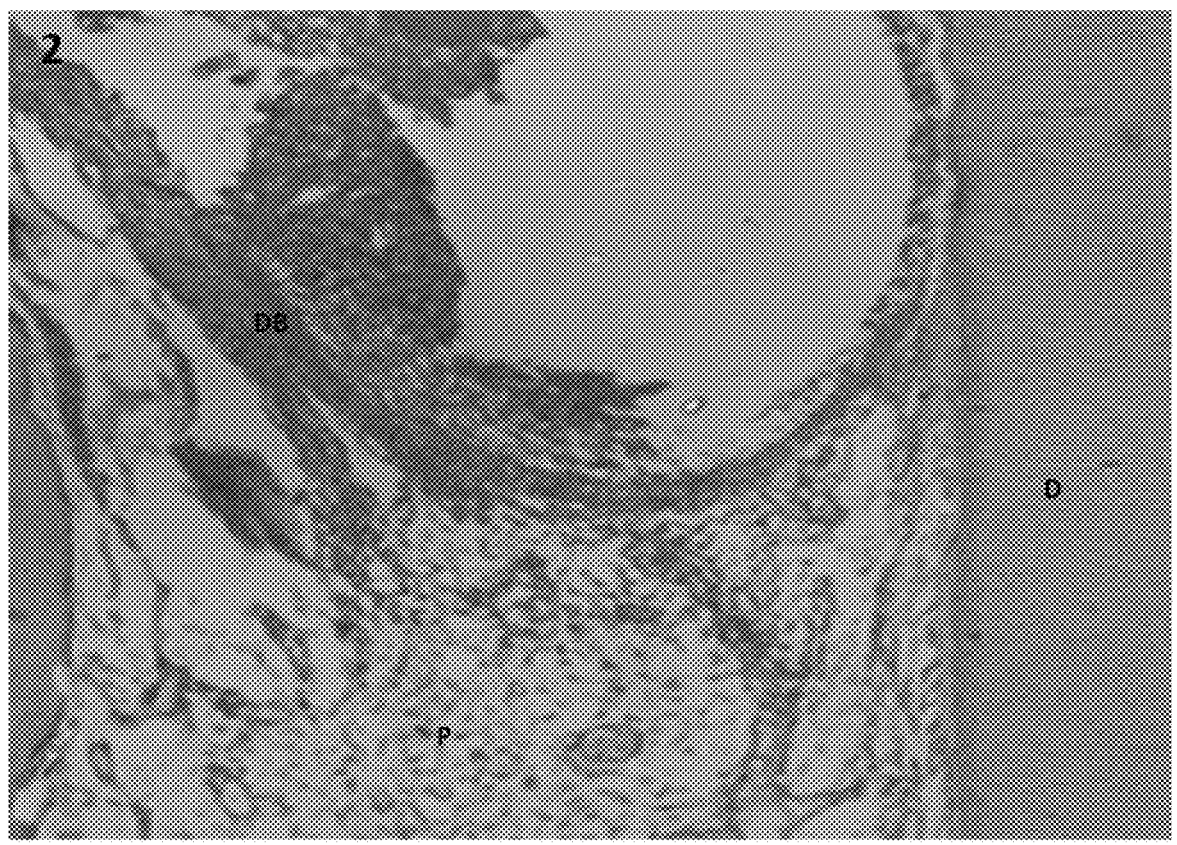
FIG. 2. Appearance of teeth treated with amelogenin-PGA after 10 days.
Figure 10:
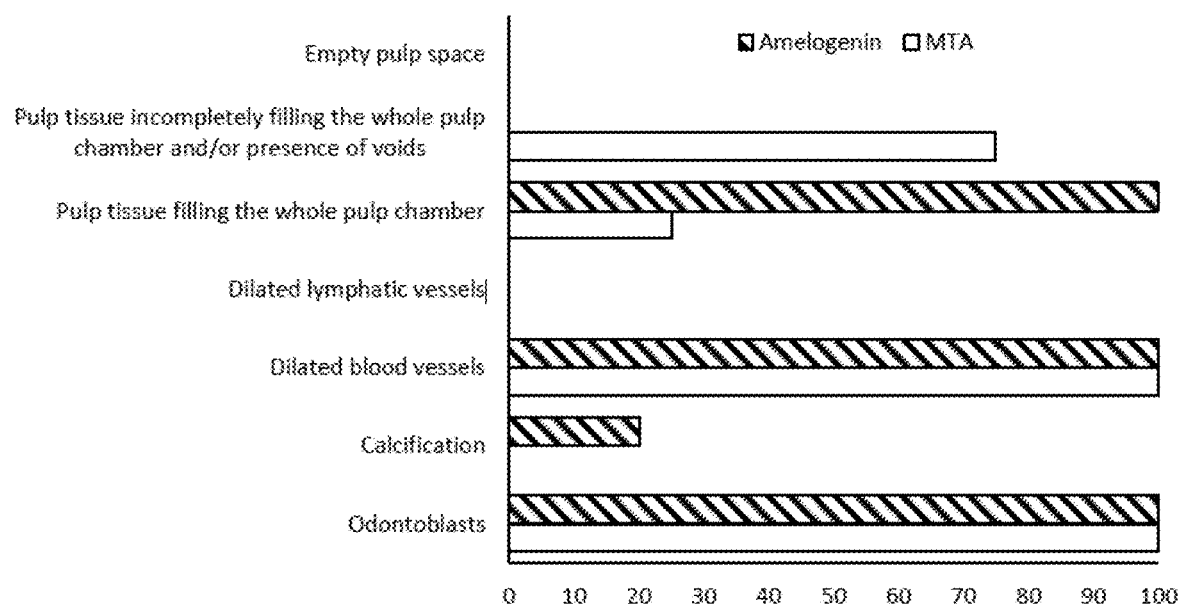
FIG. 10. Graph depicting differences at 10 days between teeth capped with amelogenin-PGA or by MTA.
Figure 11:
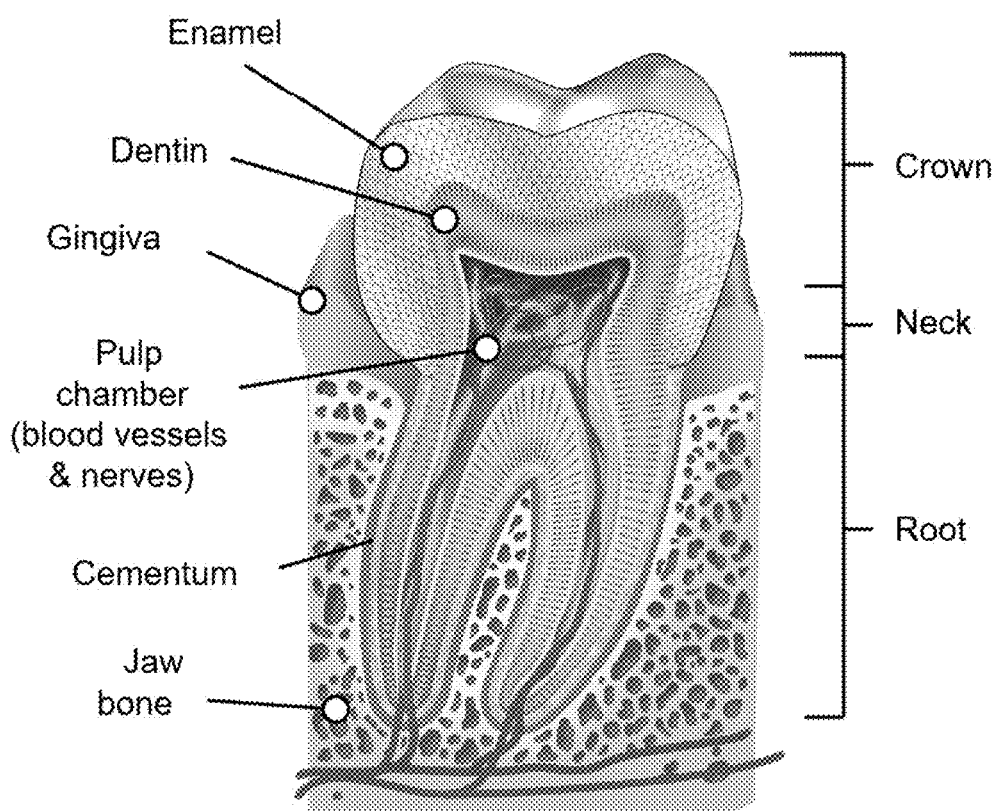
FIG. 11. Diagram of a healthy human molar showing the enamel, cementum, pulp, and dentin which make up the structure, as well as the surrounding tissues. Prior art. Author: K. D. Schroeder; *Human tooth diagram-en.svg* from Wikimedia Commons; License: Creative Commons Attribution-ShareAlike 4.0.

After 10 days various differences between teeth treated with the composition of the invention, containing recombinant amelogenin and PGA, and the conventional MTA treatment were assessed. Results are shown in Table 1 below, FIG. 10 which graphically depicts the significant improvements in tooth vitality provided by the invention, and by FIGS. 1 and 2 which show the improved histological appearance of teeth treated with amelogenin and PGA compared to those treated with MTA shown by FIGS. 5 and 6.

The histological preparation of the samples was done in the following steps:

Samples were kept in 10% neutral formalin to achieve complete fixation, then washed for 24 hours in order to remove the remnants of the fixative solution, and decalcified by 5% trichloroacetic acid. After decalcification all samples were again washed for 24 hours to remove excess acid. All samples were dehydrated using different grades of alcohol 50%, 70%, and 90% and absolute, however dehydration time depended on the density and size of each sample, lastly absolute alcohol was changed two times.

Samples were transferred from absolute alcohol to xylene until the complete replacement of the tissue by the xylene when the tissue is completely replaced with xylene paraffin ready to be infiltrated. Then samples were removed from the xylene and placed in melted dishes of paraffin wax and placed into an oven at a 60 C for 2-3 hours. After complete infiltration of the samples by paraffin; they were placed in the centre of paraffin wax box. Each tooth was sectioned in the middle of the prepared cavity bucco-lingually Serial bucco-lingual sections of the cavity were obtained using a microtome. All sections were mounted on clean slides and placed in the oven at certain temperature and then deparafanized by passing them into a two changes of xylene then two changes of absolute alcohol, then placed in 50%, 70, and 90% grades of alcohol to ensure complete dehydration, then passed through distilled water for proper staining of the samples. Serial sections were stained by hematoxylin and eosin stain and trichrome stain.

Serial sections were analysed under light microscope associated with digital camera. Each specimen was observed for: (I) calcified tissue barrier formation, complete or incomplete; (2) presence or absence of pulp tissue; condition of the present pulp, normal or altered; (4) presence of pulp inflammation; and (5) presence of pulp calcification. Analysis of the inflammatory reaction was done according to different given scores:

Score 0: Absence of inflammatory cells.
Score 1: Mild scattering of inflammatory cells with no structural damage.
Score 2: Moderate focal accumulations of inflammatory cells, no tissue necrosis with some disruption of the structure.
Score 3: Severe extensive inflammatory cell infiltrate with Replacement of tissues and abscess formation.

Analysis of dentin bridge formation was done according to given grades:
Grade 1: complete dentin bridge formation
Grade 2: the hard tissues are moderately formed
Grade 3: hard tissues are slightly formed.
Grade 4: lack of hard tissue deposition.
All samples were statistically analysed.

TABLE 1

Hard tissue formation, pulp condition and inflammatory reaction after using Amelogenin and MTA as pulp capping material after 10 days observation period.

| Variables | MTA | Amelogenin |
|---|---|---|
| Total number of teeth | 20 (50%) | 20 (50%) |
| 1—Dentin bridge formation | | |
| a—complete (grade 1) | 0.0 (0.0%) | 0.0 (0.0%) |
| b—hard tissues moderately formed (grade 2) | 0.0 (0.0%) | 16 (80%) |
| c—hard tissues slightly formed (grade 3) | 11 (55%) | 4 (20%) |
| d—lack of hard tissues formed (grade 4) | 9 (45%) | 0.0 |
| 2—Pulp status | | |
| a—presence of odontoblasts | 20 (100%) | 20 (100%) |
| b—presence of calcifications | 0.0 (0.0%) | 4 (20%) |
| c—presence of dilated blood vessels | 20 (100%) | 20 (100%) |
| d—presence of dilated lymphatic vessels | 0.0 (0.0%) | 0.0 (0.0%) |
| e—presence of pulp tissue filling the whole pulp chamber | 5 (25%) | 20 (100%) |
| f—presence of pulp tissue incompletely filling the whole pulp chamber and/or presence of voids | 15 (75%) | 0.0 (0.0%) |
| g—empty pulp space | 0.0 (0.0%) | 0.0 (0.0%) |
| 3—Presence of inflammatory cells in pulp | | |
| a—absence of inflammatory cells (score 0) | 0.0 (0.0%) | 0.0 (0.0%) |
| b—mild scattering of inflammatory cells with no sfructural damage (score 1) | 20 (100%) | 20 (100%) |
| c—moderate, focal accumulation of inflammatory cells, tissue necrosis with some disruption of the sfructure (score 2) | 0.0 (0.0%) | 0.0 (0.0%) |
| d—severe extensive inflammatory cell infiltrate with replacement of tissue and abscess formation (score 3) | 0.0 (0.0%) | 0.0 (0.0%) |

As shown by Table 1 above, after 10 days, compared to the conventional MTA treatment, the recombinant amelogenin-PGA composition of the invention formed significantly more grade 2 and grade 3 hard dentin bridge tissues and calcifications than the MTA composition. It also produced significant improvements in the vital pulp tissue which was void free in 100% of the teeth treated with the amelogenin-PGA composition compared to teeth treated with MTA in which only 25% of the pulp chambers were void free. As shown by these results the method as disclosed herein, using a mixture of recombinant amelogenin and PGA, induced the formation of a tertiary dentine mineralized barrier that efficiently sealed-in exposed dental pulp and also preserved the vitality of the tooth by preserving vital pulp in the pulp chamber. This method effectively extends the life expectancy of damaged teeth.

Figure 3:
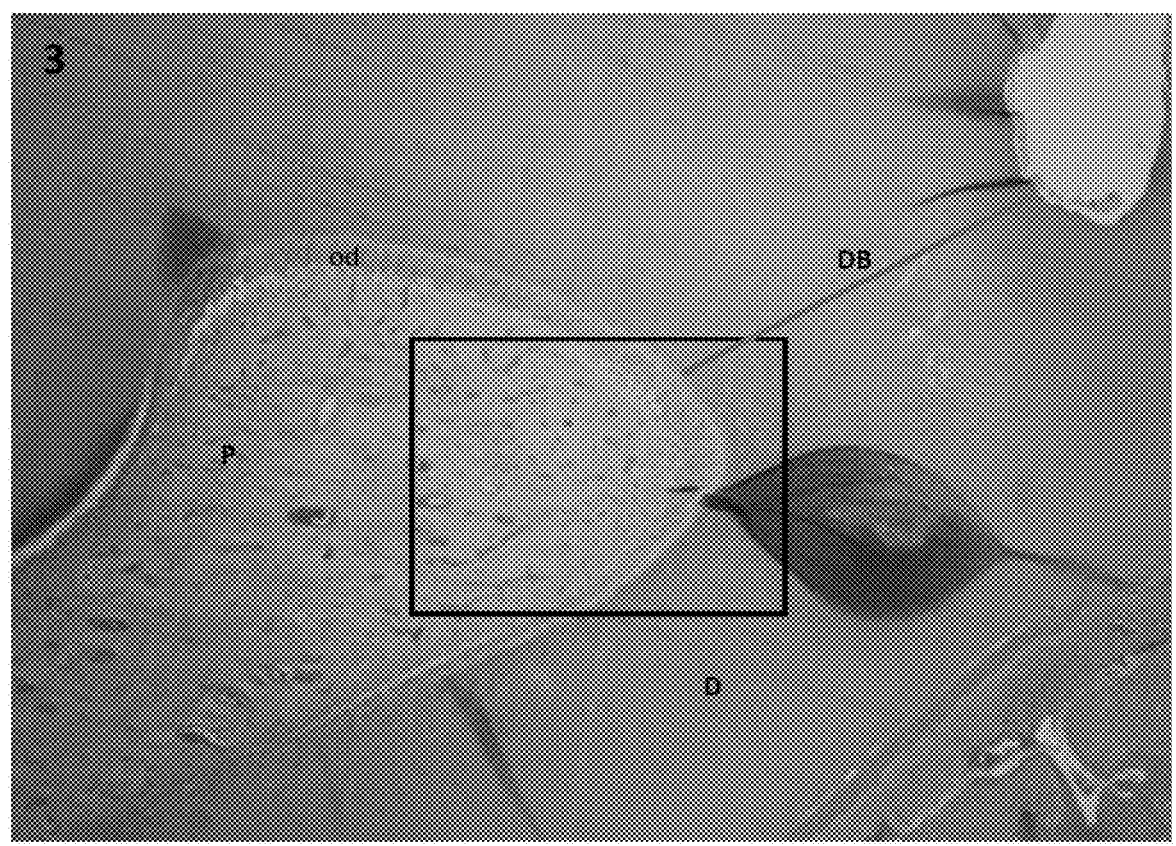
FIG. 3. Appearance of teeth treated with amelogenin-PGA after 2 months.
Figure 4:
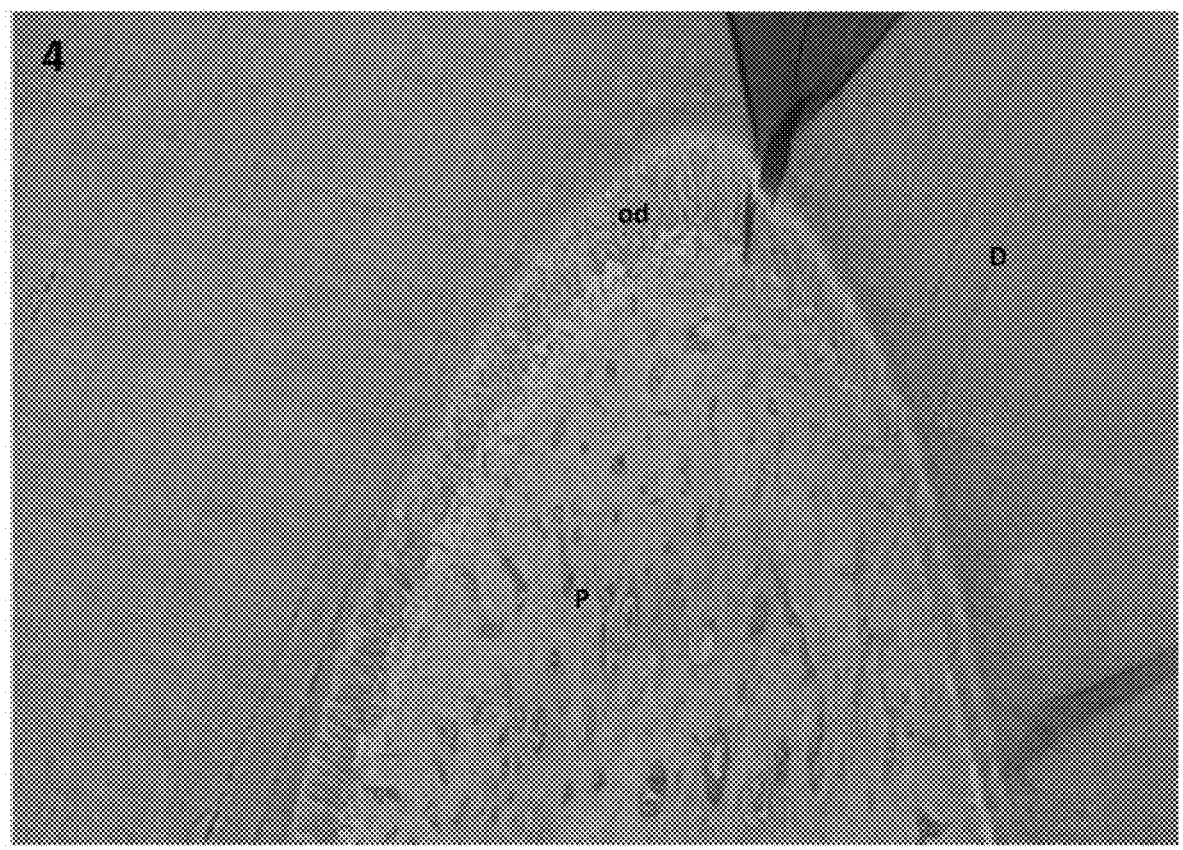
FIG. 4. Appearance of teeth treated with amelogenin-PGA after 2 months.
Figure 7:
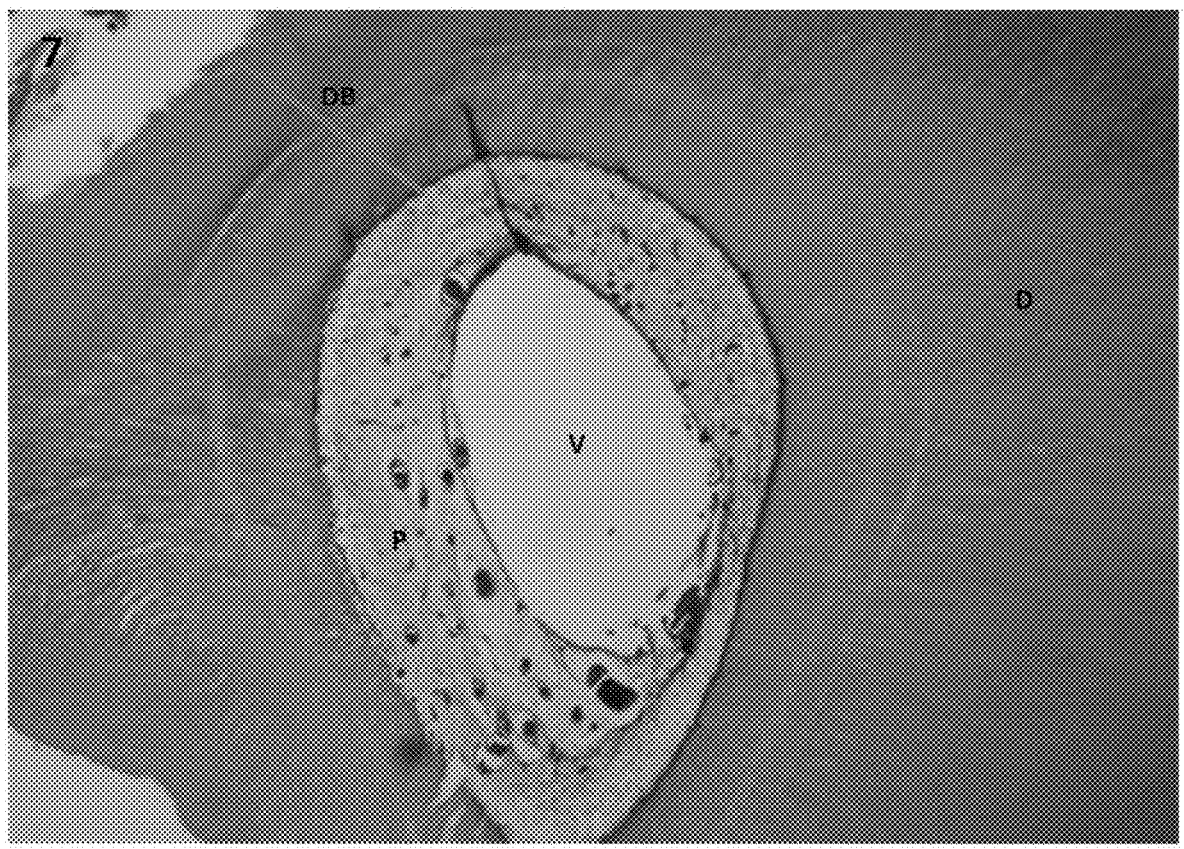
FIG. 7. Appearance of teeth treated with MTA at after 2 months.
Figure 8:
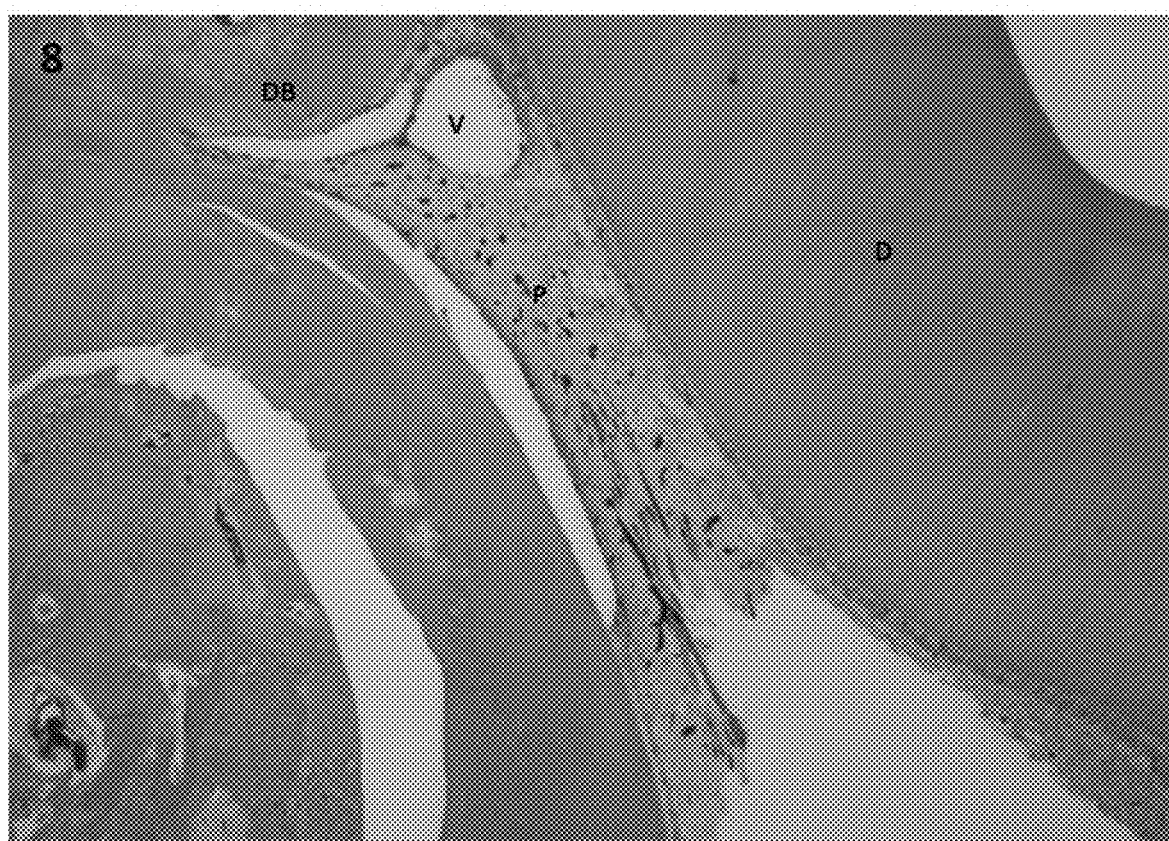
FIG. 8. Appearance of teeth treated with MTA at after 2 months.
Figure 9:
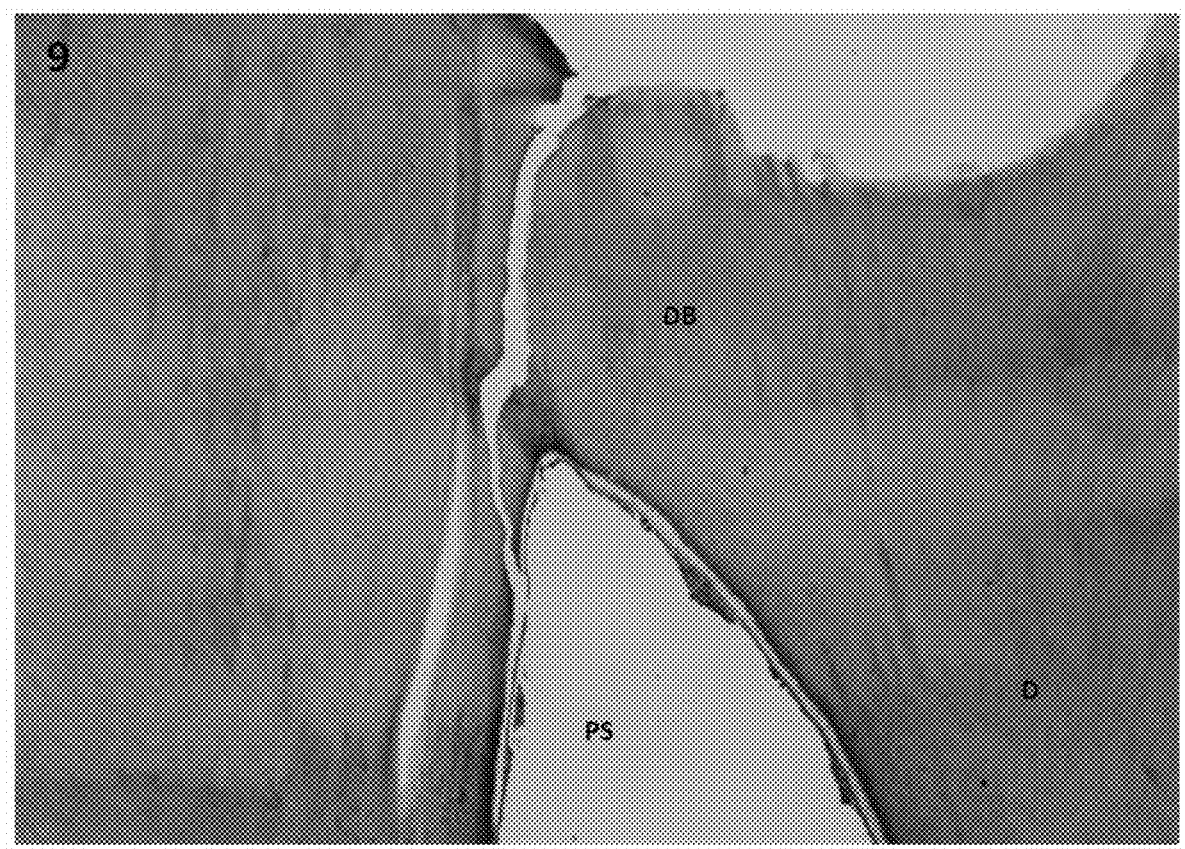
FIG. 9. Appearance of teeth treated with MTA at after 2 months.

After 2 months various differences between teeth treated with the composition of the invention, containing recombinant amelogenin and PGA, and the conventional MTA treatment were again assessed. Results are shown in Table 2 below and by FIGS. 3 and 4 which show the improved histological appearance of teeth treated with amelogenin and PGA compared to those treated with MTA shown by FIGS. 7, 8 and 9. As shown by these figures, while teeth capped with MTA instead of amelogenin-PGA can show formation of a dentin bridge, the underlying pulp tissue exhibits undesirable changes. These include dilated blood vessels and lack of contact between the MTA capping material and the underlying pulp resulting in formation of voids in the pulp tissue. In some instances, the pulp shows complete degeneration. In contrast, after 2 months, there are no voids in the teeth capped with amelogenin-PGA.

Figure 5:
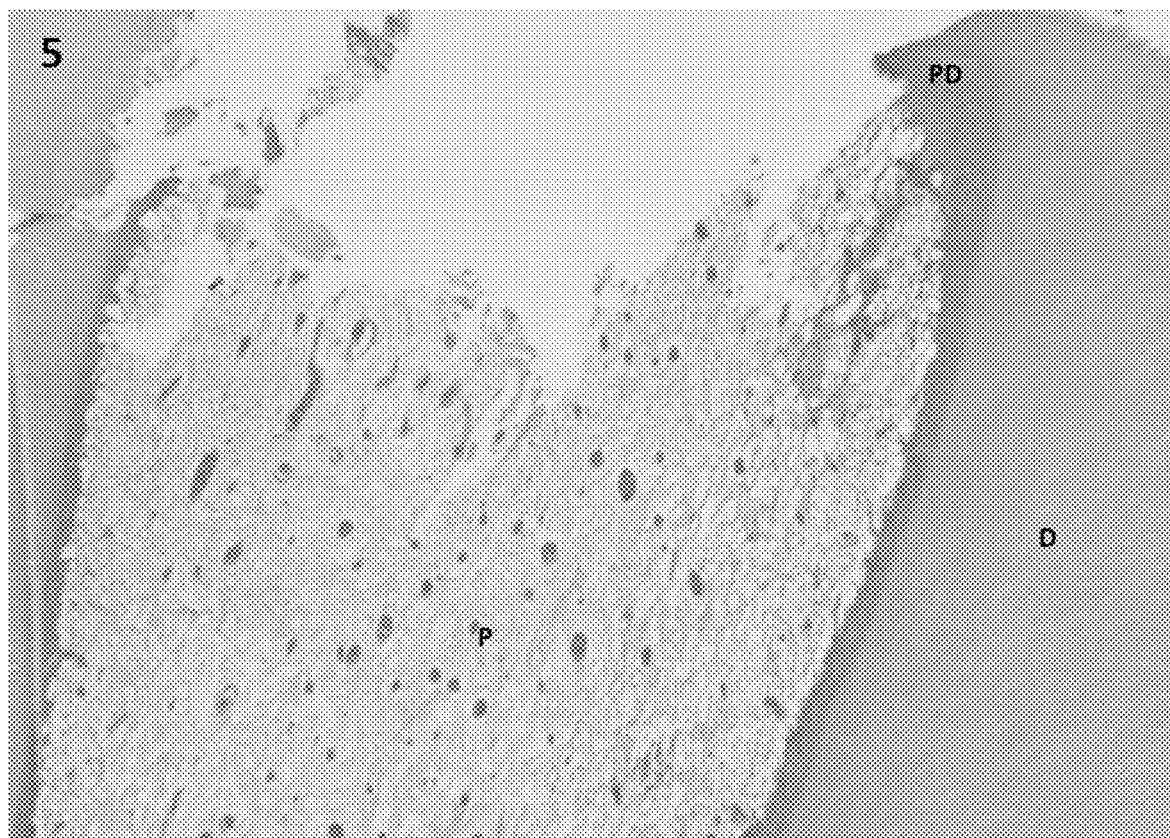
FIG. 5. Appearance of teeth treated with mineral trioxide aggregate ("MTA") after 10 days.
Figure 6:
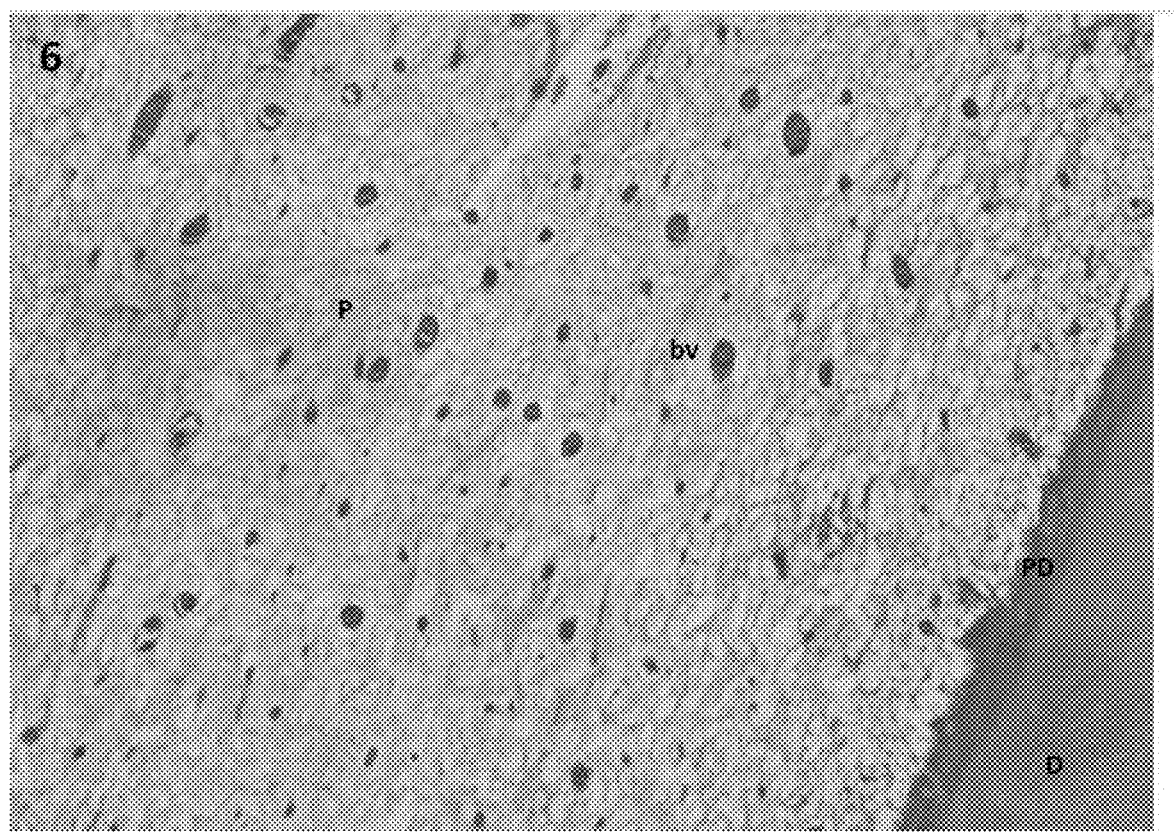
FIG. 6. Appearance of teeth treated with mineral trioxide aggregate ("MTA") after 10 days.

The histology of teeth capped with amelogenin-PGA show the formation of dentin bridge as early as 10 days placement of the material (FIGS. 1 and 2) and a thick dentin bridge by 2 months (see FIGS. 5 and 6). The underlying pulp is always in contact with amelogenin cap and the authentic pulp tissue structure is preserved in all time periods.

TABLE 2

Hard tissue formation, pulp condition and inflammatory reaction after using Amelogenin and MTA as pulp capping material after two months observation period.

| Variables | MTA | Amelogenin |
|---|---|---|
| Total number of teeth | 20 (50%) | 20 (50%) |
| 1—Dentin bridge formation | | |
| a—complete (grade 1) | 11 (55%) | 20 (100%) |
| b—hard tissues moderately formed (grade 2) | 8 (40%) | 0.0 (0.0%) |
| c—hard tissues slightly formed (grade 3) | 0.0 (0.0%) | 0.0 (0.0%) |
| d—lack of hard tissues formed (grade 4) | 1 (5%) | 0.0 (0.0%) |
| 2—Pulp status | | |
| a—presence of odontoblasts | 19 (95%) | 20 (100%) |
| b—presence of calcifications | 4 (20%) | 3 (15%) |
| c—presence of dilated blood vessels | 20 (100%) | 8 (40%) |
| d—presence of dilated lymphatic vessels | 0.0 (0.0%) | 0.0 (0.0%) |
| e—presence of pulp tissue filling the whole pulp chamber | 0.0 (0.0%) | 20 (100%) |
| f—presence of pulp tissue incompletely filling the whole pulp chamber and/or presence of voids | 16 (80%) | 0.0 (0.0%) |
| g—nearly empty pulp space | 4 (20%) | 0.0 (0.0%) |
| h—authentic pulp architecture not preserved | 0.0 (0.0%) | 0.0 (0.0%) |
| 3—Presence of inflammatory cells in pulp | | |
| a—absence of inflammatory cells (score 0) | 19 (95%) | 20 (100%) |
| b—mild scattering of inflammatory cells with no structural damage (score 1) | 1 (5%) | 0.0 (0.0%) |
| c—moderate, focal accumulation of inflammatory cells, tissue necrosis with some disruption of the structure (score 2) | 0.0 (0.0%) | 0.0 (0.0%) |
| d—severe extensive inflammatory cell infiltrate with replacement of tissue and abscess formation (score 3) | 0.0 (0.0%) | 0.0 (0.0%) |

As shown by Table 2 above, after 2 months compared to the conventional MTA treatment, the recombinant amelogenin-PGA composition of the invention form significantly 100% grade 1 hard dentin bridge formation compared to only 55% in teeth treated with the MTA composition. 100% of the teeth treated with the amelogenin-PGA composition showed pulp tissue filling the whole pulp chamber compared to 0% for teeth treated with MTA. Only 40% of the teeth treated with the amelogenin-PGA composition still exhibited dilated blood vessels compared to 100% for the MTA.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. Tooth dental pulp treatment method for indirect or direct capping of a damaged tooth comprising:
   applying a composition comprising amelogenin and propylene glycol alginate ("PGA") to a surface of a pulp containing tooth comprising open dentinal tubules or exposed pulp, wherein the amelogenin comprises an amino acid sequence that is identical to the amino acid sequence of SEQ ID NO: 2, wherein 70-90% of a total number of carboxy groups of alginic acid forming the PGA are esterified; and
   applying a permanent dental restorative on top of the applied composition comprising the amelogenin and the PGA.

2. The method of claim 1, which is a method for indirect capping and wherein the composition is applied to the open dentinal tubules.

3. The method of claim 1, which is a method of direct capping and the composition is applied to the exposed pulp.

4. The method of claim 1, further comprising, after applying the composition, applying a permanent dental restorative on top of the applied composition within a span not exceeding 24 hours.

5. The method of claim 1, wherein the tooth has been exposed to trauma associated with a dental procedure.

6. The method of claim 1, wherein the composition consists of recombinant human amelogenin and a vehicle containing the propylene glycol alginate.

7. The method of claim 1, wherein the composition further comprises a remineralization agent selected from the group consisting of a material providing calcium ions, a material providing phosphorous ions, and a material providing fluoride ions.

8. The method of claim 1, wherein said composition further comprises at least one non-amelogenin enamel matrix protein.

* * * * *